(12) United States Patent
Riopelle et al.

(10) Patent No.: US 6,417,159 B1
(45) Date of Patent: *Jul. 9, 2002

(54) METHOD OF ENHANCING EFFECT OF A NEUROTROPHIN WITH ANALOGUES OF $P75^{NTR}367\text{-}379$.

(75) Inventors: Richard J. Riopelle; Donald F. Weaver; Gregory M. Ross; Igor L. Shamovsky, all of Kingston (CA)

(73) Assignee: Queen's University at Kingston, Kingston (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/839,131

(22) Filed: Apr. 23, 1997

(30) Foreign Application Priority Data

Apr. 23, 1996 (GB) ............................................. 9608335

(51) Int. Cl.$^7$ ........................ A61K 38/00; A61K 38/10; A61K 31/55; A61K 31/426
(52) U.S. Cl. .............................. 514/2; 514/14; 514/15; 514/214; 514/365; 514/424; 514/570; 514/634; 514/648
(58) Field of Search ................................ 514/14, 2, 15, 514/214, 365, 424, 570, 634, 648

(56) References Cited

U.S. PATENT DOCUMENTS

| | | | | |
|---|---|---|---|---|
| 5,349,055 A | * | 9/1994 | Persson et al. | 530/399 |
| 5,438,121 A | * | 8/1995 | Barde et al. | 530/399 |
| 5,622,862 A | * | 4/1997 | Squinto et al. | 435/353 |

OTHER PUBLICATIONS

Rudinger, In "Peptide Hormones" (ed. J.A. Parsons) University Park Press, Baltimore, pp. 1–7, 1976.*
Ibanez et al. The EMBO J. 12:2281–2293, 1993.*
Feinstein et al, FEBS, vol. 272, Nos. 1–2, pp. 7–11, (Oct. 1990).*
Carter, et al., "Selective activation of NF–kB by nerve growth factor through the neurotrophin receptor p75", Science 272: 542–545 (1996).
Dostaler, et al., "Characterization of a distinctive motif of the low molecular weight neurotrophin receptor that modulates NGF–mediated neurite growth", Eur. J. Neuroscience 8: 870–879 (1996).
Higashijima, et al., "Conformational change of mastoparan from wasp venom on binding with phopholipid membrane", FEBS Lett. 152: 227–230 (1983).
Higashijima, et al., "Regulation of $G_i$ and $G_o$ by mastoparan, related amphiphilic peptides, and hydrophobic amines", J. Biol. Chem. 265: 14176–14186 (1990).
Huang, et al., "NMR structure and mutagenesis of the Fas (APO–1/CD95) death domain", Nature 384: 638–641 (1996).
Large, et al., "Structure and developmental expression of the nerve growth factor receptor in the chicken central nervous system", Neuron 2: 1123–1134 (1989).
Masters, et al., "Apo–3, a new member of the tumor necrosis factor receptor family, contains a death domain and activates apoptosis and NF–kB", Curr. Biol. 6: 1669–1676 (1996).
Myers, et al., "Putative cytoplasmic amphiphilic domains in the nerve growth factor/tumour necrosis factor receptor superfamily", Biochim. Biophys. Acta. 1196: 21–28 (1994).
Wakamatsu, et al., "Transferred NOE analyses of conformations of peptides as bound to membrane bilayer of phospholipid; mastoparan–X", FEBS Lett. 162: 123–126 (1983).
Hantzopoulos et al. "The Low Affinity NGF Receptor, p75, Can Collaborate with Each of the Trks to Potentiate Functional Responses to the Neurotrophins", Neuron 13:187–207 (1994).
Bothwell, "Keeping Track of Neurotrophin Receptors". Cell 65: 915–918 (1991).
Molecular Cell Biology, $3^{rd}$ ed., H. Lodish, Ed., Scientific American Books, W.H. Freeman & Co., New York, 1995, pp. 64–65.
Molecular Biology of the Cell, $2^{nd}$ ed. B. Alberts, Ed., Garland Publishing, Inc., New York, 1989, p. 276.

* cited by examiner

Primary Examiner—Gary L. Kunz
Assistant Examiner—Robert C Hayes
(74) Attorney, Agent, or Firm—Carol Miernicki Steeg; Lynn C. Schumacher; Dowell & Dowell, P.C.

(57) ABSTRACT

The present invention provides methods and compositions for enhancing the effect of a neurotrophin on a cell expressing a neurotrophin receptor. The effect is preferably neurotrophin-mediated growth and/or survival, such as neurite growth. The invention employees amphipathic compounds having a hydrophobic membrane-associating face and a hydrophilic face opposed thereto, which preferably mimic the amphipathic domain of the common neurotrophin receptor p75 from amino acid residue 367 to residue 379. Such compounds have charged moieties, polar moieties or combinations that mimic the charged and polar group relationships of $p75^{NTR}367\text{-}379$, and include but are not limited to peptide analogues thereof. The hydrophobic membrane-associating face can interact with a membrane-bound neurotrophin receptor, such as TrkA, and the opposing hydrophillic face can interact with a DNA binding protein, such as nuclear transcription factor NFkB.

18 Claims, 12 Drawing Sheets

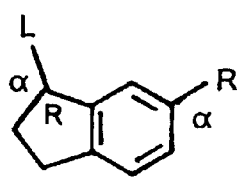
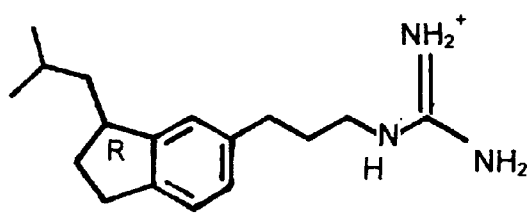
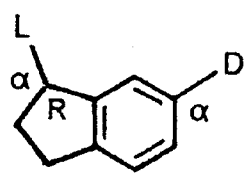
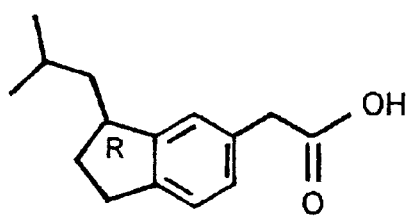
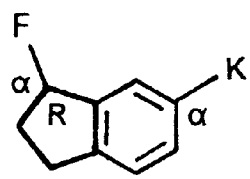
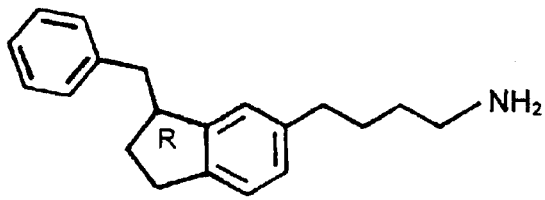
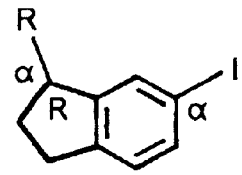
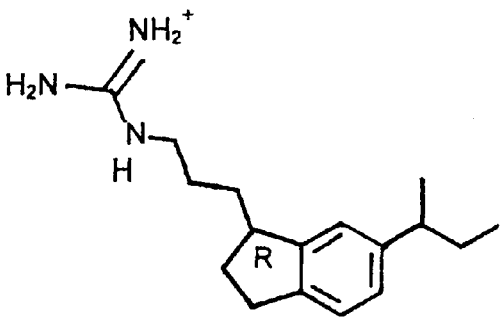
FIG. 11A
FIG. 11B

METHOD OF ENHANCING EFFECT OF A NEUROTROPHIN WITH ANALOGUES OF P75$^{NTR}$367-379.

FIELD OF THE INVENTION

The present invention relates to methods and compositions for enhancing an effect of a neutrophin, preferably, but not limited to enhancing the growth and survival promoting properties of neurotrophins, using an analogue of a portion of p75$^{NTR}$.

BACKGROUND OF THE INVENTION

The neurotrophins are a family of structurally and functionally related neurotrophic factors. The family includes prototypic member nerve growth factor (NGF), as well as brain-derived neurotrophic factor (BDNF), neurotrophin-3 (NT-3), neurotrophin-4/5 (NT-4/5) (Heumann, 1994) and neurotrophin-6 (NT-6) (Gotz et al., 1994). The neurotrophins have similar structural conformations, including three surface β-hairpin loops, a β-strand, an internal reverse turn region, and N- and C-termini, and exhibit approximately 50% amino acid sequence identity.

Neurotrophins function to promote growth and survival of certain classes of peripheral and central nervous both during development and following neuronal damage. For example, NGF is involved in the development of neurons in the peripheral nervous system, supports neuronal survival, and enhances and maintains the differentiated state of neurons. Neurotrophins can promote neurite differentiation such as sprouting or process formation, and process growth. Neurotrophins can also modulate cell motility (Anton et al., 1994), for example, both accelerate nerve process growth and decrease general cell motility. Another neurotrophin-mediated activity is induction of particular enzymes.

Furthermore, with respect to functional similarity, each of the neurotrophins can bind to a membrane-bound receptor protein (MW~75 kDa) called the common neurotrophin receptor, or "p75$^{NTR}$". Each neurotrophin also binds with higher affinity to a second membrane-bound receptor protein of the tyrosine kinase receptor (Trk) family. In particular, NGF binds selectively to the TrkA receptor, and BDNF and NT-4/5 bind selectively to the TrkB receptor. NT-3 is less selective and, though it binds primarily to the TrkC receptor, NT-3 also exhibits some binding to the TrkA and TrkB receptors (banez et al., 1993).

A variety of cell types express either p75$^{NTR}$ and/or a member of the Trk family of receptor tyrosine kinases. These include neurons, mast cells, glial cells such as astrocytes, oligodendrocytes and Schwann cells, and dysplasic or malignant cells such as neuroblastoma or melanoma cells. Cells of neuronal lineage that differentiate by extension of neurites in the presence of a neurotrophin express both a member of the Trk receptor family and lower molecular weight receptor protein p75$^{NTR}$.

Neurite growth is the best characterized differentiation response to NGF, and evidence is beginning to emerge that p75$^{NTR}$ can modulate this activity. Gene targeting studies resulting in nonfunctional p75$^{NTR}$ demonstrate reduced density of sensory and sympathetic innervation in vivo (Lee et al., 1994 a and b), possibly related to a shift to the right of dose response curves for NGF (Davies et al., 1993). The low molecular weight neurotrophin receptor p75$^{NTR}$ is a member of a family of receptors designated the NGF receptor superfamily (Krammer and Debatin, 1992; Mallett and Barclay, 1991). In addition to p75$^{NTR}$, this family includes TNFR1, TNRF2, CD30, Fas, Fas/Apo-1, Apo-3, CD40, 4-1BB, CD-27, SFV-T2, and OX-40. While these receptors have been grouped according to structural similarities in transmembrane and extracellular domains, the inventors have provided evidence supporting existence of shared pulative signalling motifs in the cytoplasmic domains (Myers et al., 1994, incorporated herein by reference). Similar to the wasp venom tetradecapeptide mastoparan (MP), p75$^{NTR}$ (rat, chick, human), human TNFR-1, and human 4-1BB have been found to have secondary structure domains with putative plasma membrane associating properties that have been implicated in intracellular signalling (Higashijima, 1983, 1990, each incorporated herein by reference).

Fas/Apo-1, TNFR1, Apo-3, and p75$^{NTR}$ all activate apoptosis via "death domains" that are rich in sequences predicted to form α-helices (Myers et al., 1994). These α-helices are potentially involved in oligomerization that mediates signalling in ligand-independent or ligand-dependent states (Huang et al., 1996). TNFR1 and p75$^{NTR}$ contain within their death domain regions, motifs that confer surface membrane associating properties (Myers et al., 1994) as determined by maximum mean hydrophobic moment (Eisenberg et al., 1984a,b), and both TNFR1 and p75$^{NTR}$ signal translocation of transcription factor NFkB (Marsters et al., 1996; Carter et al., 1996). In contrast, Apo-1/Fas, which contains a death domain but no amphiphilic sequence therein (Myers et al., 1994), does not translocate NFkB (Marsters et al., 1996). The inventors reasoned from these observations that the amphiphilic motif of p75$^{NTR}$ could be involved in NFkB activation/translocation, and thus conducted a series of experiments to determine whether the amphiphilic motif of p75$^{NTR}$ and NFkB interact directly.

Based on knowledge of their biological actions, neurotrophins have been considered for therapeutic use in neurological disorders characterized by loss of neurons and/or loss of connectivity. Such disorders include stroke, cerebral and spinal cord injury, a host of neurodegenerative disorders, the most prevalent of which is Alzheimer's disease, and a variety of peripheral nerve disorders, most notably those associated with diabetes mellitus and cancer chemotherapy.

These are limitations to use of neurotrophins for therapy of neurological disorders. Such limitations relate to the prohibitive costs of production of recombinant human neurotrophins, their stability in vivo, the routes of administration, and penetration of the blood-brain and nerve-brain barriers.

To circumvent such limitations, stable small molecule neurotrophin agonists or stable small molecule modulators of neurotrophin levels or neurotrophin effects would be desirable.

SUMMARY OF THE INVENTION

It is an object of the present invention to provide methods and compositions for enhancing an effect of a neurotrophin, preferably enhancing the growth and survival promoting properties of a neurotrophin.

It is a further object to provide low molecular weight analogues of p75$^{NTR}$ 367–379 useful as therapeutic agents for in situ treatment of certain neurological disorders.

It is a yet another object to provide low molecular weight analogues of p75$^{NTR}$ 367–379 useful for ex vivo treatment of cells. Such ex vivo uses include diagnostic applications, assays wherein various factors are screened, and applications wherein cells, e.g., hematopoientic cells, are treated prior to their reintroduction to a patient.

Utilizing peptide analogues of a putative amphiphilic domain of p75$^{NTR}$, the inventors have discovered that these analogues have biophysical and biochemical properties in MP (Sequence ID No. 5) that they are taken up into cells, that the amphiphilic properties and polar group relationships of p75$^{NTR}$ 367–379 analogues influence signalling pathways involved in neurite growth by NGF-responsive cells of neuronal lineage, and that these analogues depend upon the functional expression of TrKA to exert their influence. The findings suggest that p75$^{NTR}$ participates by interaction of its amphiphilic domain with a Trk receptor to modulate neurite growth.

In the broadest aspect, the present invention provides a method for enhancing the effect of a neurotrophin on cells having a plasma membrane and expressing a neurotrophin receptor. The method comprises providing an effective compound having an effective number of charged moieties spaced thereon and, when in close proximity to the plasma membrane, an amphipathic conformation comprising a substantially hydrophobic membrane associating face and a substantially hydrophilic face. The method includes exposing the cells for an effective period of time to an effective amount of the compound in the presence of the neurotrophin for enhancing the effect of the neurotrophin on the cells. In a first preferred embodiment, the compound is a peptide or peptidomimetic. In a second preferred embodiment, the cells are of a neuronal lineage, and the effect is growth and/or survival. In a third preferred embodiment, the neurotrophin is nerve growth factor (NGF) and the receptor is TrkA.

In this aspect of the invention, the effective compound is an analogue of an effective putative amphiphilic domain of p75$^{NTR}$, and the neurotrophin receptor is selected from the nerve growth factor receptor superfamily.

In some embodiments, the analogue is a peptide chain comprising amino acid residues and having an amphipathic portion. The amphipathic portion includes a substantially hydrophobic membrane associating face and a substantially hydrophilic face. Further, in certain embodiments, the amphipathic portion is an α-helix having a periodicity in hydrophobicity of the amino acid residues effective to form the substantially hydrophobic membrane associating face and the substantially hydrophilic face. The α-helix may comprise a sequence of about eleven amino acid residues. In other embodiments, the peptide chain may have substantially hydrophobic membrane associating face and a substantially hydrophilic face that are couple by a turn. At least one of the faces may be a β-strand or other organized secondary structure; for example, the membrane associating substantially hydrophobic face may be a β-strand.

A preferred peptide analogue in this aspect of the invention comprises a peptide sequence LDALLAALRRIQR (Sequence ID No. 1) and the neurotrophin receptor is tyrosine kinase family member Trk A.

In other embodiments of this aspect of the invention, the effective compound is not a peptide, but mimics amphipathic properties and functional effects of p75$^{NTR}$ 367–379.

The invention provides a method for enhancing the effect of a neurotrophin on cells having a membrane, a DNA binding protein in their cytoplasm, and expressing a neurotrophin receptor. The method comprises providing an effective compound, the compound having an effective number of charged moieties spaced thereon and, when in close proximity to the membrane a conformation comprising a membrane associating substantially hydrophobic face and a substantially hydrophilic face for associating with the DNA binding protein. The method includes exposing the cells for an effective period of time to an effective amount of the compound in the presence of a neurotrophin for enhancing growth or survival of the cells.

In another aspect of the invention there is provided an amphipathic compound for enhancing an effect of a neurotrophin on cells having a membrane and expressing a neurotrophin receptor. The compound comprises a substantially hydrophobic portion for associating with the membrane and a substantially hydrophilic portion comprising charged moities, polar moities or combinations thereof for interacting with a factor partaking in a mechanism of the enhancing effect including but not limited to nuclear transcription factors.

The present invention provides an amphipathic peptidomimetic compound for enhancing an effect of a neurotrophin on cells having a membrane and expressing a neurotrophin receptor. The compound comprises a substantially hydrophobic portion of associating with the membrane and a substantially hydrophilic portion comprising charged moieties, polar moieties or a combination of both for interacting with a factor partaking in a mechanism of the enhancing effect.

In another aspect of the invention there is provided a method for enhancing neurotrophin-mediated growth and/or survival of cells having a plasma membrane and expressing a neurotrophin receptor. Preferably, the cells are of a neuronal lineage. The method comprises exposing the cells for an effective period of time to an effective compound.

The peptide compound is a peptide analogue of an effective putative amphiphilic domain of p75$^{NTR}$ and the peptide analogue is a linear peptide chain comprising a sequence of at least about level amino acid residues. The peptide compound may have a periodicity in hydrophobicity of the amino acid residues effective to form a membrane associating amphipathic α-helix portion in close proximity to the plasma membrane. The α-helix portion has a substantially hydrophobic face and a substantially hydrophilic face with the compound having an effective number of charged moieties spaced thereon. In an alternate preferred embodiment, other organized secondary structural motifs cooperate to form a substantially hydrophobic membrane associating domain and a substantially hydrophilic domain.

The present invention provides a method for enhancing an effect of a neurotrophin on cells having a plasma membrane and expressing a neurotrophin receptor. The cells may be of a neuronal lineage and the effect may be nerve growth factor-mediated neurite growth. The method comprises exposing the cells for an effective period of time to a medium comprising an effective amount of a peptide having a membrane associating amphipathic α-helix in close proximity to said plasma membrane. The peptide may have a sequence LDALLAALRRIQR (Sequence ID No. 1).

In another aspect the invention provides a method for enhancing an effect of a neurotrophin, preferably nerve growth factor-mediated neurite growth in cells of a neuronal lineage. The method comprises providing cells of a neuronal lineage having a surface membrane and being capable of expressing a neurotrophin receptor. The method includes exposing the cells for an effective period of time to a medium comprising an effective amount of nerve growth factor and a peptide having a sequence LDALLAALRRIQR (Sequence ID No. 1) wherein the sequence forms a membrane associating amphipathic α-helix in close proximity to the surface membrane.

In this aspect of the invention the neurotrophin receptor is selected from the tyrosine kinase family and more particularly is tyrosine kinase family member TrkA.

The present invention provides a use for an effective compound for enhancing an effect of a neurotrophin in cells having a plasma membrane and expressing a neurotrophin receptor. Preferably, the cells are of a neuronal lineage and the effect is nerve growth factor-mediated neurite growth. The use for the effective compound comprises providing a medium comprising the effective compound, wherein the compound is an analogue of an effective putative amphiphilic domain of p75$^{NTR}$. The cells are exposed to an effective amount of the compound for an effective period of time in the presence of a neurotrophin for enhancing neurite growth in the cells. The analogue may be a linear peptide chain comprising a sequence of about eleven amino acid residues having an effective number of charged moieties spaced thereon and having a periodicity in hydrophobicity of the amino acid residues so that said compound has a membrane associating amphipathic α-helix portion in close proximity to said plasma membrane. The α-helix portion has a substantially hydrophobic face and a substantially hydrophilic face.

In this aspect of the method the peptide analogue may have an amino acide sequence LDALLAALRRIQR (SEQ. ID NO.: 1) or a functional equivalent thereof.

BRIEF DESCRIPTION OF THE FIGURES

The method and compositions of the present invention will now be described, by way of example only, reference being had to the accompanying drawings, in which:

FIG. 11A shows four prophetic examples of peptidomimetics, showing chirality, that are expected to enhance neurotrophin effect(s) in accordance with the present invention.

FIG. 11B illustrates the same molecules as shown in FIG. 11A but shows the fully drawn amino acid side chains.

DETAILED DESCRIPTION OF THE INVENTION

Figure 1A:
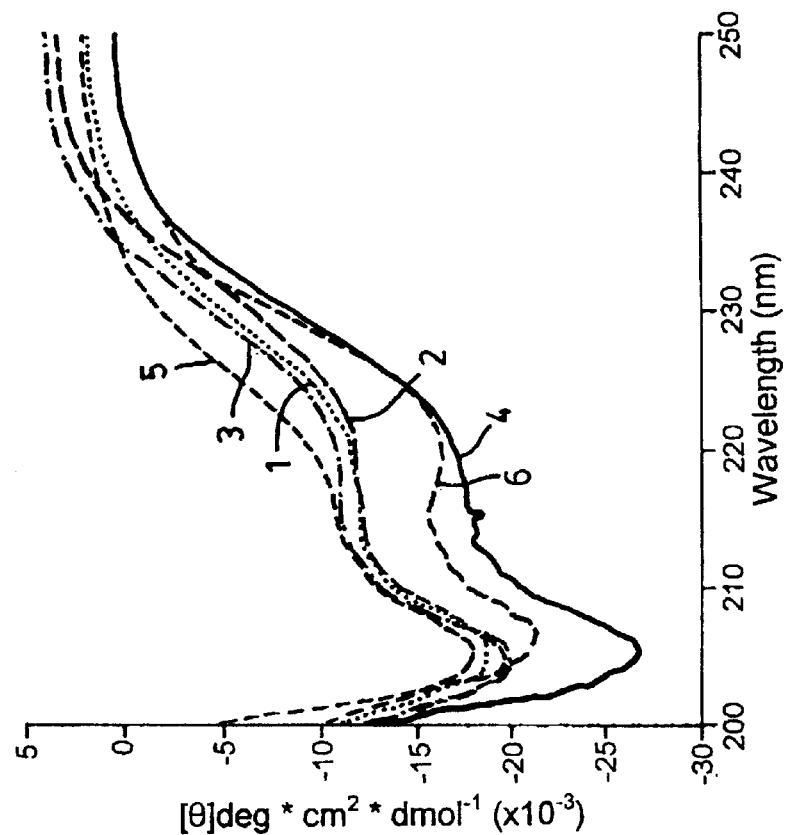
FIG. 1A compares the circular dichroism spectra of mastoparan (MP) and active and inactive peptides in an aqueous solution at 22° C.
Legend:
1. R9 51.8 μM (Sequence ID No. 2)
2. R3 51.4 μM (Sequence ID No. 1)
3. R10 51.7 μM (Sequence ID No. 3)
4. MP50.0 μM (Sequence ID No. 5)
5. YR3 50.1 μM (Sequence ID No. 6)
6. R4 52.8 μM (Sequence ID No. 7)

The present invention provides compounds having the functions of R3 peptide as described below, and methods of enhancing the effect of a neurotrophin using such a compound. R3 is a peptide having 13 amino acid residues that are identical to the sequence of residues 367–379 of rat p75$^{NTR}$. As described below, substitutions may be made to particular residues of R3, resulting in functional differences. Analogues of R3 that have qualitatively the same functions are encompassed by the invention, though there may be minor quantitative differences in efficacy. Such qualitative functions include ability to enhance the effect of a neurotrophin, and particularly ability to enhance neurotrophin-mediated cell growth and/or survival. Such functions also include ability to interact with or bind to cell membrane, and ability to interact with or bind to transcription factor NFkB. Structurally, analogues of R3, whether peptide or non-peptide compounds, are amphipathic. That is, they have a substantially hydrophobic membrane associating face and a substantially hydrophilic face.

In R3, the substantially hydrophobic membrane associating face and the substantially hydrophilic face are oriented relative to each other as opposite faces of an α-helix. In peptide analogues of R3, residue substitutions may be made so that charged or polar residues are positioned on the hydrophilic face, and uncharged or non-polar residues are positioned on the hydrophobic face. Deviations from this positioning scheme are encompassed by the invention only so far as qualitative function is retained. Peptide analgoues of R3 may be longer or shorter than R3 so long as qualitative function as defined above is retained. Similarly, peptide analogues of R3 according to the invention are not limited to having only the twenty commonly occurring amino acids, and amino acid residues may be modified, so long as R3-like function is maintained. A peptide analogue of R3 is not limited to α-helix. For example, a peptide analogue may have as substantially hydrophobic membrane associating β-strand portion or any other organized secondary structural motif such as for example β-sheet, β-turn or γ-turn that is linked to a substantially hydrophilic β-strand portion, or another functional conformation.

Moreover, the invention is not limited to peptide analogues of R3. Rather, the invention encompasses any compound with amphipathic properties wherein a first face of the compound is able to associate with or be anchored in a cell membrane and a second face display charged or polar moieties, wherein the compound enhances the effect of a neurotrophin. In some embodiments of the invention, the compound is a small molecule. In some embodiments, the compound comprises a polymer portion; any convenient polymer backbone may be employed.

In Morgan et al., 1989 (incorporated herein by reference), peptide mimetics are defined as "structures which serve as appropriate substitutes for peptides in interactions with receptors and enzymes. The mimetic must possess not only affinity, but also efficacy and substrate function." For purposes of this disclosure, the terms "peptidomimetic" and "peptide mimetic" are used interchangeably according to the above-excerpted definition. That is, a peptidomimetic exhibits function(s) of a peptide, without restriction of structure. Peptidomimetics of the present invention, i.e., analogues of R3, may include amino acid residues or other moieties which provide the functional characteristics described herein.

As described previously, R3 can be taken up by cells. The ability to be taken up by cells is desirable for compounds of the invention. In some embodiments, a compound of the invention may have structural characteristics that permit it to be taken up directly. In other embodiments, a compound of the invention may be linked to a carrier that permits uptake by cells. When inside the cell, certain carriers dissociate from the compound having R3-like properties. Certain other carriers are chemically cleaved from the compound having R3-like properties.

Below, the inventors provide prophetic examples of compounds of the invention. Compounds of this type may be employed in methods of the invention.

PART A
Characterization of a Distinctive Motif of the Low Molecular Weight Neurotrophin receptor that modulates Neurotrophin_Mediated Neurite Growth
Mateials and Methods
Peptide Synthesis
Peptides were custom synthesized on solid phase using Fast-moc chemistry by the Core Facility for Protein/DNA Chemistry (Department of Biochemistry, Queen's University, Kingston, Canada). Prior to use, the synthetic products were purified by reverse phase high performance liquid chromatography (HPLC) on a PEP-S™ column (Pharmacia), and their amino acid compositions and sequences were verified.

Iodination of Peptides

Labeling of all tyrosinated peptides for uptake studies were carried out using IODO-BEADS™ (Pierce). Briefly, 5 $\mu$g of the desired peptide was iodinated at pH 7.4, at room temperature, and separated from free iodide by selective elution from a C-18 SEP PAK LIGHT™ (Waters-Millipore) in 80% $CH_3CN$, 1.0% trifluoroacetic acid. The solvent was removed at room temperature under a stream of nitrogen. Specific activity of labeled peptide was 50–65 cpm·pg$^{-1}$.

Uptake Protocol

Stock solutions of [$^{125}$I]-labeled peptides (final concentration 5 of 10 $\mu$M, specific activity 50–800 cpm·pmol$^{-1}$) were prepared in RPMI medium with 10% fetal calf serum. Uptake was initiated by adding the peptide to the cell suspension in RPMI 1640 with 10% fetal calf serum, maintained at 37° C. Cell-associated label was determined by counting the cell pellet obtained by microcentrifuging an aliquot (100 $\mu$l containing 1-3×10$^5$ cells) of the cell suspension through a layer of silicone oil. The silicone oil was 3:1 mixture of dibutyl phthalate:dinonyl phthalate (Fluke Chemie, Switzerland) with a density of 1.027 (Drevon et al., 1977).

The uptake versus were corrected for "adsorption" of peptides to the cell surface at zero time. This was assessed by determining label that remained associated with cells removed immediately after the addition of [$^{125}$I]-peptide and washed by 2 cycles of centrifugation at 150 $\mu$g for 5 minutes and resuspension in peptide-free tissue culture medium. At the indicated times, cold chase values were obtained by removing an aliquot (500 $\mu$l) of the cell suspension for centrifugation at 150×g for 5 minutes, followed by resuspension in its initial volume of RPMI+10% fetal calf serum containing 50 $\mu$M (10×original) unlabeled peptide. The cell suspension was then returned at 37° C. for a further 30 minutes. At the end of this time, cell-associated label was determined as above.

Circular Dichroism (CD) Spectroscopy

Circular dichroism (CD) spectra were recorded at 22° C. on a computer-controlled Jasco J-600 spectropolarimeter, using a 1-cm quartz cell. Analyses were carried out in an aqueous environment, and in a membrane-mimetic environment using trifluoroethanol (Ananthanarayanan et al., 1992). Scans were averaged eight times at a scan speed of 50 nm·min$^{-1}$. The means-residue molar ellipticity [$\theta$] was normalized for peptide concentration, and expressed in deg cm$^2$·dmol$^{-1}$.

Acid Phosphatase Assay of Cell Survival

This is a colorimetric assay which measures the lysosomal enzyme acid phosphatase to determine cell number (Connolly et al., 1986) modified by Ueda et al. (1994) for use with cultured neuronal cells. Medium was removed gently from PC12 or PC12$^{nnr5}$ cells cultured in 96 well plates and well were washed once with 200 $\mu$l PBS. Then 100 $\mu$l of buffer containing 0.1M sodium acetate pH 5.5, 0.1% TRITON™ X-100, and 10 mM p-nitrophenyl phosphate (Sigma 104 phosphatase substrate) was added to each well. Plates were placed in a 37° C., 5% $CO_2$ incubator for 3 hours. The reaction was stopped by the addition of 10 $\mu$l/well of 1N sodium hydroxide and the colour development measured at 405 nm using a microplate reader (Titertek). The first column on each plate contained no cells (buffer only) and was used as a blank. The relationship between cell number and enzyme activity was linear over the range 1000 to 15,000 cells.

Assay of Motochondrial Function

A colorimetric assay measuring the number and respiratory activity of surviving cells (Mossman, 1983) was used to monitor the effect of the synthetic peptides on PC12 cells. Culture plates (96-233, Flow, flat bottom) were seeded with 4,000 cells per well and received treatment identical to the cells read for neurite formation. At the indicated times, the medium was removed from the wells with a Pasteur pipette and replaced with 110 $\mu$l of RPMI+10% fetal calf serum containing 0.45 mg·ml$^{-1}$ MTT (Sigma) and the plate were returned to a humidified, 5% $CO_2$ incubator for 4 hours. 100 $\mu$l of 0.4N HCl in isopropanol was then added to each well with trituration (approximately 50 times) to solublize the formazan. The plates were read 10 minutes later in a flow Titertek Multiskan equipped with a 570 nm filter, and the optical density values obtained were corrected for cell-free blank. In each experiment, the values are the average of at least triplicate determinations normalized to its control. The MTT dye conversion was linear with number of viable cells over the range seeded, i.e. 2000 to 10,000 cells per well.

Assays of Neurite Growth

PC12 cells or PC12$^{nnr5}$ cells (Loeb et al., 1991) were seeded on poly-D-lysine-coated (0.1 mg·ml$^{-1}$, overnight) 96-well microculture dishes (Falcon) at approximately 800 cells per well with RPMI with 10% fetal calf serum. Peptides were added to replicate wells 48 hours before, or at the time of, addition of NGF. NGF was prepared by the method of Mobley et al. (1976) and used at 1–2 nM. Other additives were diluted at least 100-fold and added to the wells as described. At various times following incubation at 37° C., 5% $CO_2$, wells were scored for neurite-bearing cells by serial counting of representative circumferences of each well.

Dissociated cells enriched for sensory neurons from DRG of ED8 chick or ED19 rat were prepared as described in detail previously (Sutter et al., 1979a). ED19 rat DRG dissociates were not pre-plated pror to bioassay. Cells were seeded into wells of Terasaki plates previously treated with poly-D-lysine at 700–900 per well in supplemented Ham's F12 medium with 2.5% fetal calf serum and NGF at concentrations between 0.04 and 40 pM. The cells were incubated with the additives as described at 37° C., 5% $CO_2$, and scored at various times for neurite growth by counting all cells on the lower horizontal surface of the wells, which is approximately 15% of the surface area of the top of the tapered wells.

A Leitz Diavert inverted microscope with phase optics was used to score neurite growth. For both PC12 cells and sensory neurons, a neurite was scored as such if its calibre from origin to terminal was approximately the same and the length was equal to or greater than 1.5 cell body diameters.

Binding and Uptake of [$^{125}$I]NGF

PC12 cells were removed from culture dishes with CMF, washed, and incubated at a concentration of 10$^6$ per ml in Hepes-Krebs-Ringer (HKR) buffer buffer with 1 mg·ml$^{-1}$ BSA for 90 minutes at 37° C. in the presence of 40 pM [$^{125}$I]NGF in the absence and presence of excess unlabeled NGF, and in the absence and presence of R3 peptide. Aliquots of 100 $\mu$l were removed in replicates and mircocentrifuged at 10,000×g for 1 minute. Supernatants were removed, tips were cut from the microcentrifuge tube and counted in a gamma counter. Specific binding was defined as the difference between binding of the ligand in the absence and presence of unlabeled NGF, and fractional specific binding in the absence and presence of R3 peptide was compared. Studies of [$^{125}$I]NGF uptake into PC12 and PC12$^{nnr5}$ cells were carried out in the absence and presence of 10 µM R3 peptide and following a 24-hour exposure of PC12 cultures to 10 µM R3 peptide. Cells were eposed to 20 pM or 0.2 nM [$^{125}$I]NGF for periods of time up to 240 minutes (steady state) at 37° C. The cells were then briefly acid-washed as described by Bernd and Greene (1984), and aliquots were prepared for gamma counting as described. NGF was radioiodinated as described in Sutter et al. (1979b).

[$^{125}$I]NGF Affinity Cross-linking

PC12 cells treated with R3 peptide or with no peptide, were harvested from the plates as described for receptor binding studies, washed and incubated with [$^{125}$I]NGF for 2 hours at 4° C. For TrkA cross-linking, bis-(sulfosuccinimidyl) suberate (BS$^3$) was added to a final concentration of 0.4 nM (in 20 µl), and incubated for 20 min at 25° C. For p75$^{NTR}$ cross-linking, N-hydroxysulfosuccinimide (NHS; final concentration 2.0 nM) and 1-ethyl-3-(3-dimethylaminopropyl)carbodiimide (EDC; final concentration 5 mM) were each added in 20 µl and incubated for 30 min at 25° C. Upon completion of the cross-linking reaction cells were washed three times in HKR buffer with BSA at 4° C. to remove excess free radiolabeled ligand and reagents.

Immunoprecipitation

Immunoprecipitation was utilized for affinity cross-linking studies and for studies of phosphorylation of TrkA. Following exposure to NGF and peptide R3, cells were solublized in 1 ml of lysis buffer containing 10 mM Tris-HCl pH 7.4, 150 mM NaCl, 10% glycerol, 1% NP-40, 0.01 mg·ml$^{-1}$ aprotinin, 0.5 mM orthovanadate, 0.5 µg·ml$^{-1}$ leupeptin, and 2 mM phenyl-methyl-sulfonylfluoride (PMSF) at 4° C. for 15 min. Cellular debris was removed by centrifugation, and antibodies (final concentration 20 µg·ml$^-$1) were added to the supernatant and incubated at 4° C. for 2 h with constant mixing. Either Protein A-SEPHAROSE (for TrkA) or goat anti-mouse agarose (for p75$^{NTR}$) pre-equilibrated in lysis buffer was added to each sample (50 µl of a 50% solution) and incubated at 4° C. for 2 h. The immunoprecipitated proteins were then washed with lysis buffer and eluted from the affinity gels using reducing SDS sample buffer. Antibodies were generously supplied by E. Shooter (p75$^{NTR}$; Stanford) and W. Mobley (TrkA; University of California, San Francisco).

SDS-PAGE and Autoradiography

[$^{125}$I]NGF cross-linked proteins from cells or immuno-precipitated proteins were solublized in reducing SDS sample buffer at 95° C. for 10 min. Samples were separated on a modified Laemmli (1970) discontinuous acrylamide gel system using a 4% SDS-PAGE stacking gel and a gradient urea polyacrylamide separating gel ranging from 4.5% acrylamide/18% urea to 7.5% acrylamide/48% urea. The gel system was found to give an appropriate molecular weight range and resolution for unambiguous identification of both monomers and dimers of TrkA and p75$^{NTR}$. Gels were subsequently fixed and process for autoradiography using a −70° C. exposure with Kodak XAR film and manual processing.

TrkA Phosphorylation

TrkA phosphorylation was performed by a modification of the method of Kaplan et al. (1991 a and b). PC12 cells were harvested as described and suspended at a concentration of 10$^7$ ml in HKR buffer. NGF (100 ng·ml$^{-1}$) was added and the cell suspension was incubated for 30 min at 37° C. and pelleted at 4° C. The cells were solublized with lysis buffer, and TrkA protein was immunoprecipitated as described. Proteins were fractionated by 7.5% SDS-PAGE, and transferred to nitrocellulose for immunoblot analysis as described (Harlow and Lane, 1988). Phosphoproteins were visualized using anti-phosphotyrosine clone 4G10 (UBI) as described in the supplier's product literature.

Statistical Analysis

Data were analysed using one-way ANOVA followed by the Student t-test.

RESULTS

Biophysical Properties of p75$^{NTR}$ Peptide Homologues

Figure 1B:
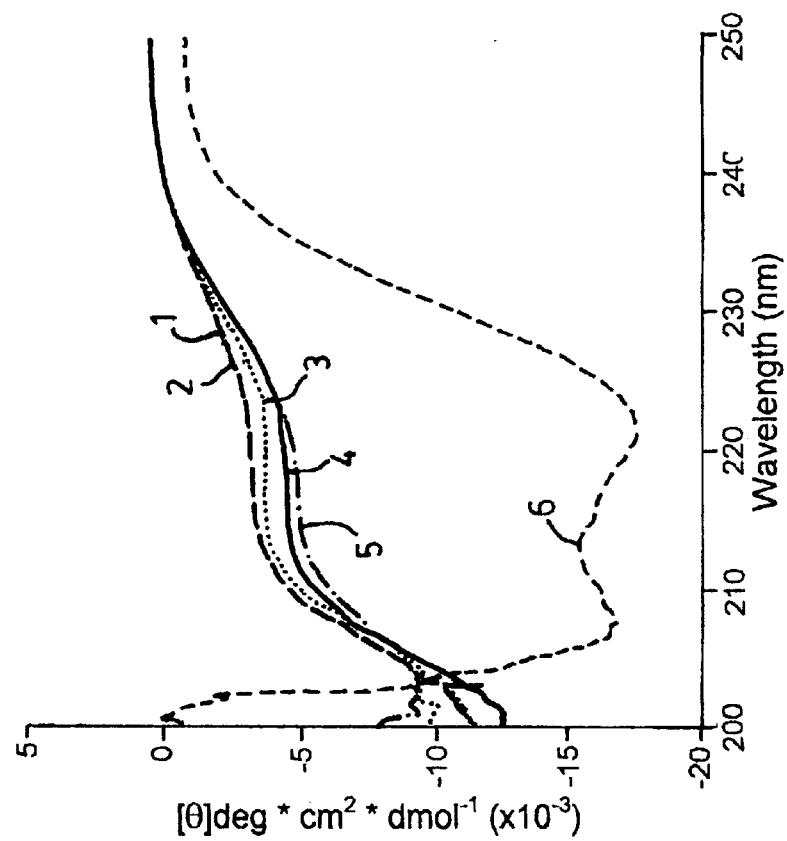
FIG. 1B compares the circular dichroism spectra of mastoparan and active and inactive peptides in trifluoroethanol at 22° C., the legend being the same as for FIG. 1A.
Figure 2:
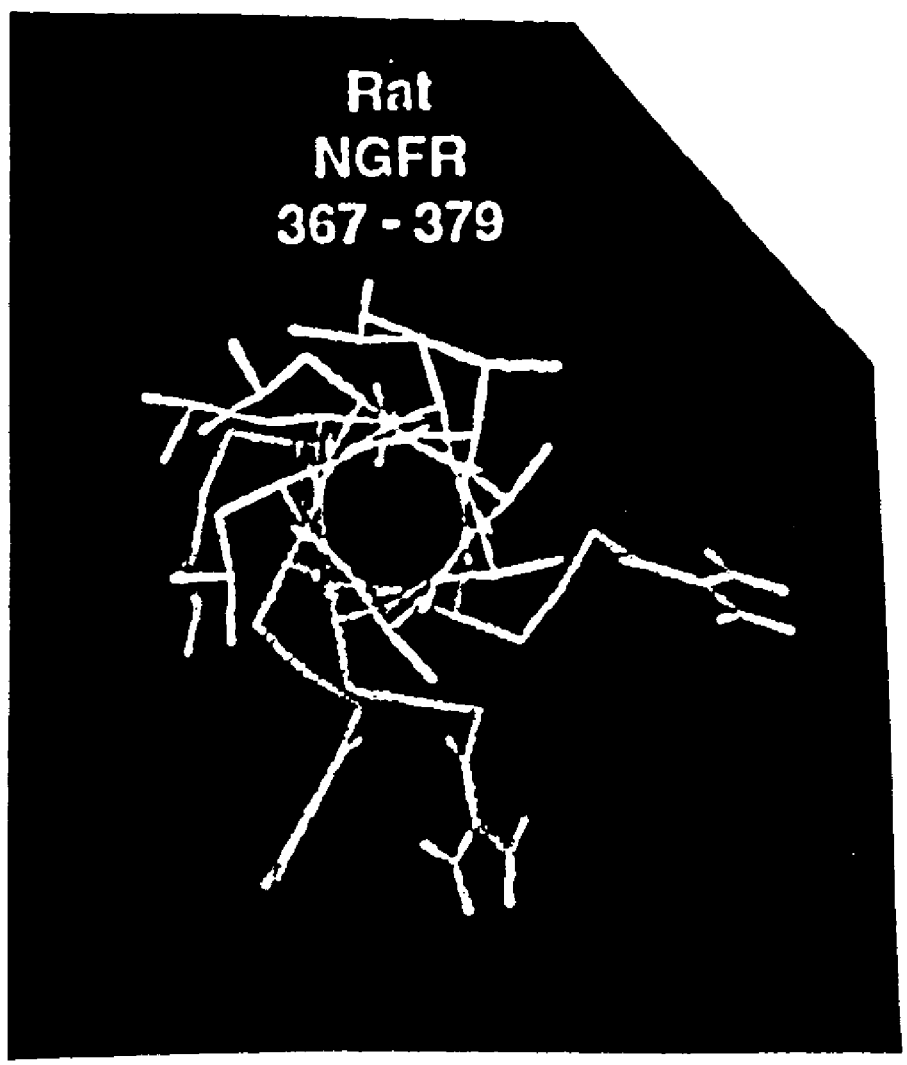
FIG. 2 illustrates amphiphilicity of a computer-simulated peptide motif of rat p75$^{NTR}$ 367–379 viewed parallel to the long axis of the α-helix. The program BIOGRAF (Molecular Simulations, Inc., San Diego, Calif.) was used to construct identified membrane surface associating regions with minimization carried out using an AMBER force field, the α-helix being constrained, and the amino acid side chains being free to find their most stable conformations.

FIGS. 1A and 1B depict CD spectra of MP and synthetic peptide analogues of p75$^{NTR}$367–379. The synthetically produced peptide R3 is identical to rat p75$^{NTR}$367–379. The amphiphilicity of a computer-simulated peptide motif of rat p75$^{NTR}$367–379 viewed parallel to the long axis of the α-helix is shown in FIG. 2, as disclosed in Myers et al., 1994. Peptide R4 represents a hybrid, comprising R3 linked via its amino terminus to an 11-amino acid peptide homologue of the inner transmembrane domain of p75$^{NTR}$ (Large et al., 1989); peptide R9 is an A-10-R substitution in R3; peptide R10 is an R-11-I substitution in R3. In aqueous solution (FIG. 1A), the CD spectrum of MP was typical of non-helical forms with a negative band around 200 nm. As described by Higashijima et al. (1983, 1990), MP adopted an alpha-helix conformation at approximately the 20% level in aqueous solution, and this conformation was similar to that observed with peptides R3, R9, and R10. As would be predicted by the addition of eleven amino acids of the transmembrane domain of p75$^{NTR}$ to R3, the conformation of peptide R4 was more typical of the alpha-helical form with negative bands at 208 nm and 222 nm. As suggested by the computational studies (Myers et al., 1994) and as demonstrated for MP in the presence of phospholipid and membrane-mimetic solvent (Higashijima et al., 1983, 1990), MP and the peptides with CD spectra in aqueous solution similar to MP (R3, R9, R10) also displayed the typical alpha-helical form when dissolved in trifluoroethanol (FIG. 1B). The tyrosinated peptide analogue of R3 (Y-R3), displayed a CD spectrum in aqueous and non-polar environments identical to R3. Similary, tyrosinated peptide analogues of R9 and R10 had CD spectra similar to R9 and R10 (data not shown).

R3 Analogues Accumulate in the Intracellular Compartment

To ensure that the influence of R3 analogues on neurite growth was consistent, both temporally and quantitatively, with accumulation in the intracellular compartment, kinetics of cell association utilizing dilution/cold chase experiments with peptide analogues were carried out. Following incubation, aliquots of the cell suspension were either centrifuged immediately (association paradigm) or washed by dilution and centrifugation in a 10-fold excess of unlabeled peptide (uptake paradigm). Where [$^{125}$I]-labeled tyrosinated peptides were utilized, label that was resistant to dilution and cold chase with unlabeled peptide accumulated in PC12 cells. R3 and [$^{125}$I]Y-R3 had approximately the same effects on NGF-mediated neurite growth by PC12 cells (data not shown) and similar CD spectra (FIGS. 1A and 1B). The time course of association of [$^{125}$I]Y-R3 with PC12 cells indicated that uptake was apparent and half-maximally saturated with 30 minutes, fully saturated at 20 pmol/10$^6$ cells by approximately 10–20 hours, and remained resistant to chase by excess unlabeled R3 for up to 50 hours. Cell association of [$^{125}$I]R4 with PC12 cells displayed kinetics that, unlike Y-R3, did not suggest an uptake process, and at no time was cell association resistant to chase (defined as uptake) detectable (data not shown). Table 1 summarizes uptake data on all peptide analogues utilized in the study under various conditions, and indicates that times to half-maximal uptake and maximal uptakes were similar. Evidence confirming previous studies (Gill et al., 1991, Nakahata et al., 1990) that MP was taken up by cells was provided by demonstrating that this peptide had a stimulatory effect on NGF-mediated c-fos mRNA induction by PC12 cells during a one-hour exposure, as quantified by northern blot analysis (data not shown).

Figure 3:
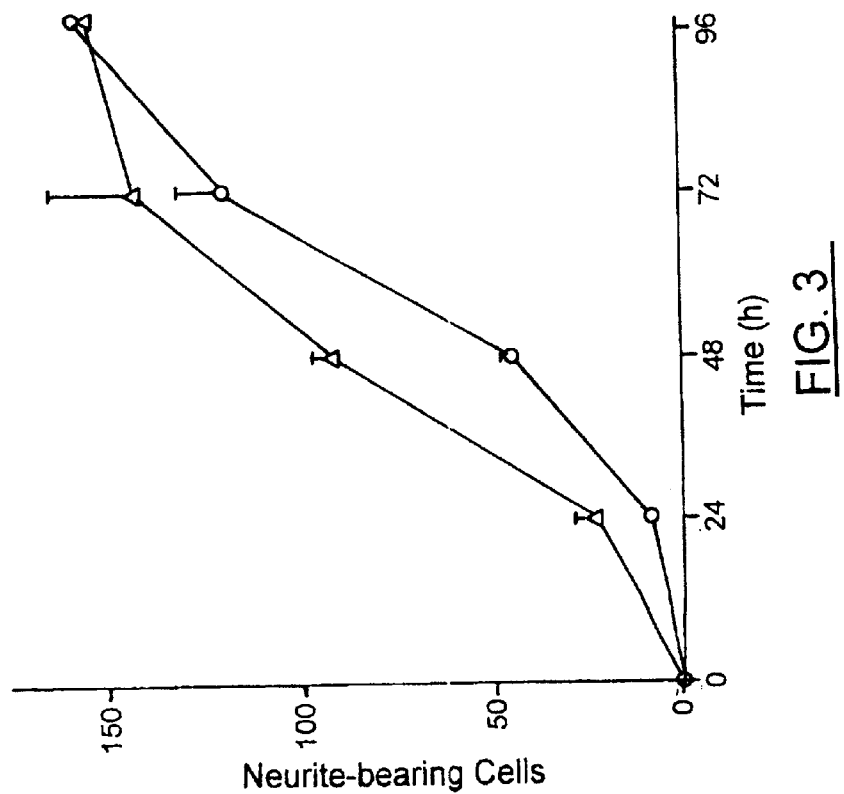
FIG. 3 illustrates the influence of peptide R3 on time dependence of neurite growth by PC12 cells. At each time point, a representative circumference of the microculture well was scored for neurite growth. Results are expressed as M±SEM (N=6 wells for each point), o-NGF along; Δ-peptide R3 10 μM plus NGF.

The R3 Peptide Influences NGF-mediated Neurite Growth

Where the neurite growth-promoting effects of NGF on naive PC12 cells were quantified as a function of time, co-incubation with R3 (10 $\mu$M) enhanced temporally the neurite growth response, but the peak response was not altered (FIG. 3). Differences between R3 plus NGF and NGF alone were seen at 24 hours and were highly significantly different (p<0.001) by 48 hours. Where the mutant cell line PC12$^{nn5}$ which expresses p75$^{NTR}$ and low levels of TrkA (Loeb et al., 1991) was utilized as a target, NGF had no effects on neurite growth in the absence or presence of the R3 peptide (data not shown).

Figure 4:
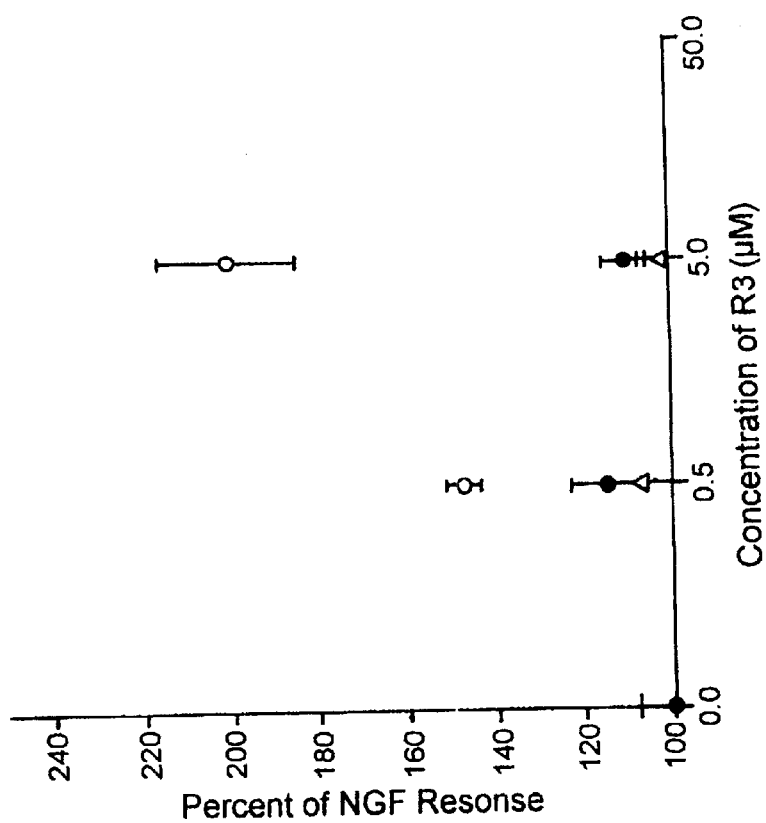
FIG. 4 shows the concentration-dependent influence of peptides on NGF-mediated neurite growth by PC12 cells. Peptides R3 (○), R4 (●), and mastoparan (Δ) were co-incubated with PC12 cells in the presence of NGF, and wells were scored at various times between 30 and 58 hours for neurite growth. Results are expressed as mean±standard error of the mean (M±SEM) percent of the NGF response at 44 hours; n=6 wells for each point.

The effect of R3 on the NGF-mediated neurite growth response by PC12 cells were dose-dependent (FIG. 4). At all concentrations of R3, the maximal effect was observed at approximately 40–48 h, and these effects were saturable at concentrations between 5 and 50 $\mu$M. At concentrations of 50 $\mu$M and above, the peptide tended to precipitate out of aqueous solution with time.

Figure 5B:
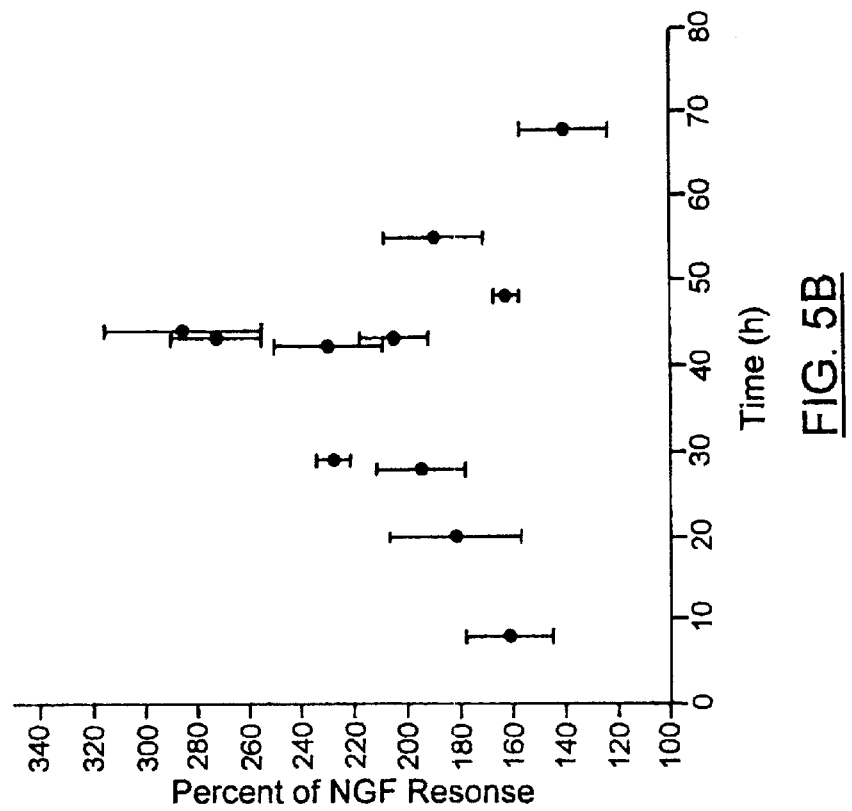
FIG. 5B shows data from an assay depicting influence of co-incubation (●) with peptide R3 on NGF-mediated neurite growth by embryonic day 8 (ED8) chick dorsal root ganglion (DRG) neurons. Results are expressed as M±SEM (N=6 wells per point) percentage of control response as in FIG. 5A.
Figure 5A:
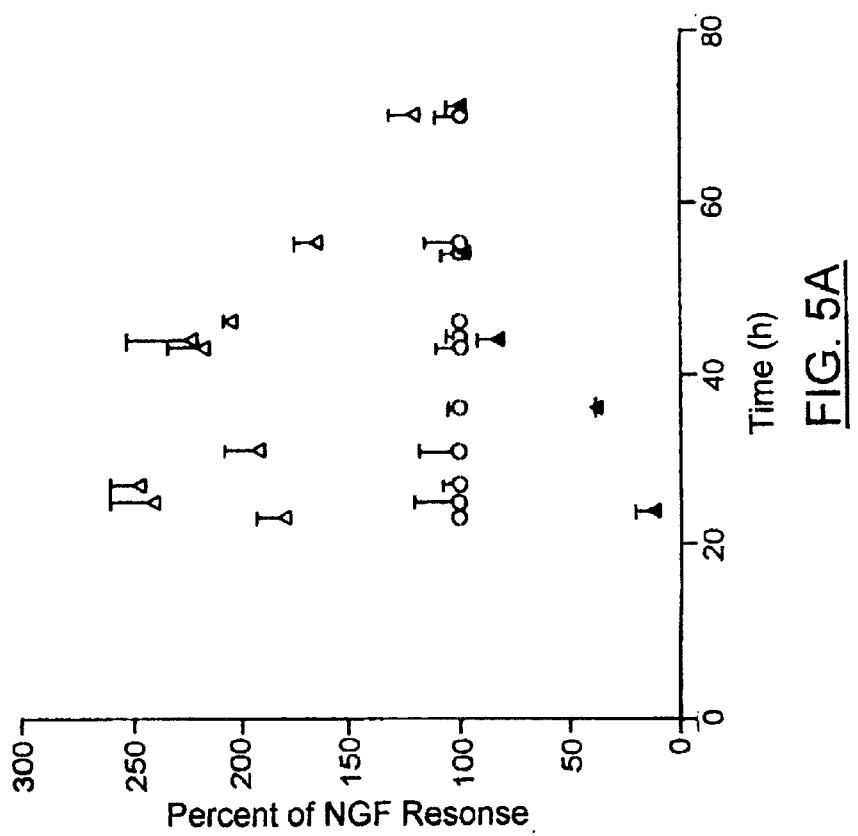
FIG. 5A shows composite data from three assays depicting influence of pre-incubation(▲) and co-incubation (Δ) with peptide R3 (10 μM) on NGF-mediated neurite growth by PC12 cells. Results are expressed as M±SEM (N=6 wells per point) percentage of control response (NGF alone—○). For pre-incubation studies with PC12 cells, peptide R3 was added to the wells 48 hours before addition of NGF and retained in the wells during NGF exposure.

Concentration-dependent effects were seen only with peptide R3. Peptide R4, which did not accumulate intracellularly, did not enhance NGF-mediated neurite growth (FIG. 4). However, MP, which accumulates in the intracellular space (Gill et al., 1991; Nakahata et al., 1990), and which had a stimulatory effect on NGF-mediated c-fos mRNA induction in PC12 cells, did not significantly influence the NGF effect on neurite growth by PC 12 cells at any concentration (FIG. 4); at a concentration of 50 $\mu$M both MP and R4 were cytotoxic.

Where R3 was present in PC12 cultures for 24 or 48 hours prior to addition of NGF, the neurite growth response to NGF was inhibited transiently relative to co-incubation and to no pretreatment (FIG. 5A) (p<0.001 versus NGF co-incubation alone at 24 and 36 hours).

The enhancing effect of R3 co-incubation on NGF-mediated neurite growth was also observed with 8-day embryonic chick DRG neurons (FIG. 5B) and with embryonic 19 day rat DRG neurons (data not shown). The neurite growth response of chick sensory neurons appeared somewhat earlier and was more robust than that observed with PC12 cells (p<0.01 at all times except 68 hours).

Figure 6B:
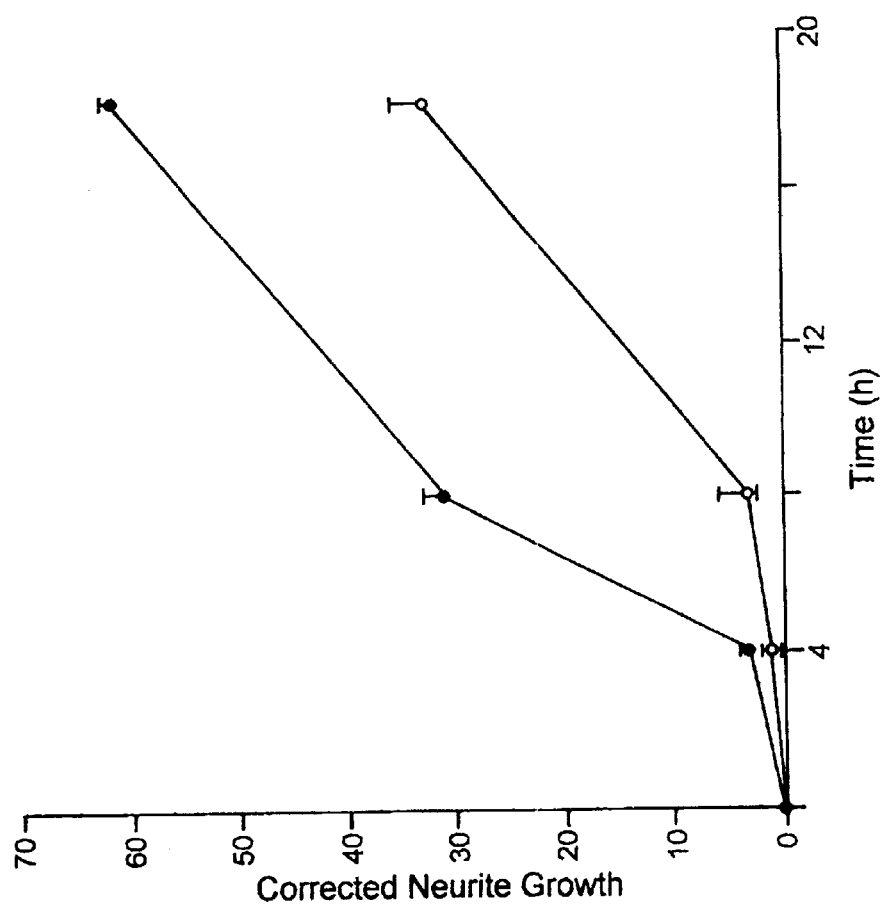
FIG. 6B displays time dependent influences of R3 on NGF-mediated neurite growth of ED8 chick sensory neurons. ED8 chick DRG neurons were seeded onto poly-D-lysine treated plates in medium with NGF (4 pM) in the absence (open circles) and presence (closed circles) of R3 peptide (10 μM). Neurite growth was quantified at the times indicated, and differences were significant (p<0.05, Student t-test) by 8 hours. Results are expressed as corrected neurite growth (M±SEM) defined as NGF minus no NGF, and (NGF and R3) minus (R3 and no NGF).
Figure 6A:
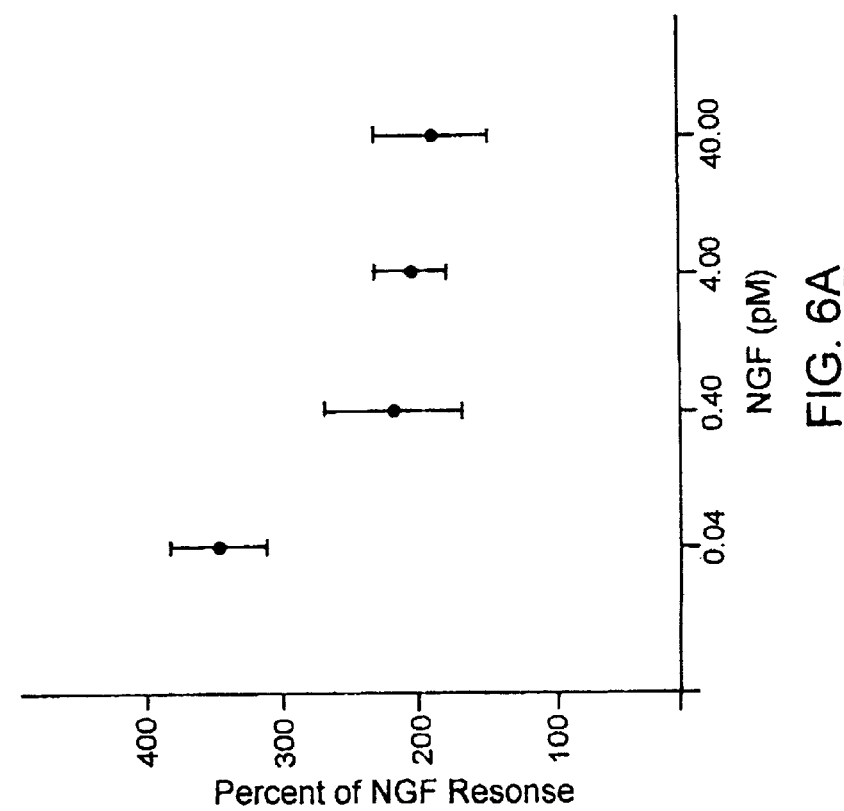
FIG. 6A displays concentration dependent influences of R3 on NGF-mediated neurite growth of ED8 chick sensory neurons. ED8 chick DRG neurons were seeded onto poly-D-lysine-treated plates in medium with NGF at the indicated concentrations, in the absence (control) and presence (treatment) of 10 μM R3 peptide. Neurite growth in the presence of R3 quantified at 16–20 hours differed significantly from its paired control (p<0.05, Student t-test) at all of the NGF concentrations assayed. Results are expressed as a ratio of treatment to its control; data points are the mean of four experiments, and error bars represent standard error of the mean. In control wells, neurite growth was 5.5±2.1 (0.04 pM), 14.0±6.1 (0.4 pM), 31.7±8.7 (4 pM), 44.8±8.6 (40 pM).

Taking advantage of the lower dose requirements and the more rapid responsiveness to NGF by embryonic chick DRG neurons, the NGF dose-dependency of the R3 peptide effect on neurite growth enhancement was characterized using these primary neurons. As depicted in FIG. 6A, the effect of R3 on NGF-mediated neurite growth was dependent on NGF concentration and was most robust at lower concentrations at times up to 25 hours (p<0.01).

The effect of the R3 peptide on early events in neurite growth was also examined using ED8 chick DRG neurons. The presence of R3 markedly increased the response to NGF between 4 and 8 hours (FIG. 6B). After 8 hours the number of neurite bearing cells in the absence or presence of R3 increased at approximately the same rate. To ensure that the effects of R3 peptide on primary neurons and on PC12 cells were mechanistically similar, influence of the peptide on cell cycle departure by PC12 cells which might accelerate the response to NGF by these cells (Lopresti et al., 1992) was analyzed. Mitochondrial succinate dehydrogenase activity, as quantified by the MTT assay of cell proliferation (Mossman, 1983), was not enhanced by the presence of R3, and the peptide had no influence on PC12 cell mitochondrial respiration in the presence of NGF (data not shown).

Thus, similar effects of the R3 peptide occurred with PC12 cells (no non-neurons), ED8 chick DRG cells (neuron-enriched), and ED19 rat DRG cells (mixed cultures).

The R3 Peptide Does Not Influence Cell Survival at These Experimental Dosages of NGF To exclude the possibility that the effects of R3 on neurite growth in the experiments described above were indirect and mediated by an influence on cell survival, PC12 and PC12$^{nnr5}$ cells were exposed to serum free conditions in the absence and presences of NGF, and in the absence and presence of R3. Table 2 illustrates that cell survival was lower in serum-free conditions than in the presence of serum whether or not R3 was present, and that R3 had no influence on NGF-mediated survival of low- or high-TrkA expressing PC12 cells whether or not it was present. Nor was there any difference in NGF-mediated survival whether R3 exposure occurred before or at the same time as NGF exposure. However, the inventors expect that, at other NGF concentrations, R3 and analogues thereof will have effects on cell survival, particularly p75-mediated apoptosis, per the discussion below.

Structure-Activity Relationships of R3 for Neurite Growth

Within the amphiphilic domain of p75$^{NTR}$, the chick and rat peptide sequences differ at primary sequence sites 372 and 376, being rat A-372 and chick V-372, and rat R-376 and chick K-376 (Large et al., 1989). These differences in non-polar and cationic groups had no bearing on enhancement of NGF-mediated neurite growth since R3 (identical to rat p75$^{NTR}$ 376–379) was effective on chick embryo DRG neurons, rat PC12 cells, and rat DRG cells.

Alterations of the amphiphilicity of p75$^{NTR}$ 367–379 would be predicted to influence the biological activity. Where non-polar amino acid I-11 in R3 (I-377 in p75$^{NTR}$) was substituted with a cationic group R-11 to give peptide R10, the maximum mean hydrophobic moment ($\mu_H$) (Eisenberg et al., 1984 a,b) was reduced from 0.75 to 0.42 and the predicted sequence type changed from a surface-of-membrane to a globular protein. At 40–50 hours in vitro, this substitution reduced the biological effect of peptide R10 by approximately 70% (p<0.05) relative to R3 on enhancement of the NGF-mediated neurite growth response by DRG cells (Table 3). At 46 hours, a similar observation (p<0.05) was made using PC12 cells (data not shown).

Angular and distance relationships between ionic groups in the amphiphilic domain of rat p75$^{NTR}$ 367–379 would also be predicted to alter the biological properties of the domain. The hydrophobic moment is a measure of the amphiphilicity of a segment of a protein. From the 3-dimensional structure of the protein segment the hydrophobic moment is calculated, according to Eisenberg et al.

$$\mu_H = \left( \left[ \sum_{n=1}^{N} H_n \sin\delta_n \right]^2 + \left[ \sum_{n=1}^{N} H_n \cos\delta_n \right]^2 \right)^{1/2}$$

where N is the number of amino acid residues, and $H_n$ is the hydrophobicity of the nth residue. For a helical (i.e., periodic) structure specified by m (the number of residues per turn), $\delta_n = 2\pi n/m$, where $\delta_n$ is the angle in radians at which the nth side chain emerges from the helical axis. Where a non-polar group A-10 was substituted for R-10 in R3 (R-376 in p75$^{NTR}$) to give a peptide designated R9, $\mu_H$ (Eisenberg et al., 1984 a, b) was reduced from 0.75 in R3 to 0.66 in R9 and at the time of peak responsiveness (40–50 hours), approximately 40% (p<0.05) of the biological effect relative to R3 on NGF-mediated neurite growth by DRG cells was lost (Table 3). A similar trend that did not achieve statistical significance was observed using PC12 cells (data not shown).

Effects of Magnesium and Pertussis Toxin on R3 Peptide Effects $Mg^{+2}$ blocks stimulatory effects of MP on steady-state GTPase activity and on dissociation of GDP from free alpha subunits of G-proteins (Higashijima et al., 1990). In the PC12 cell assay of NGF-mediated neurite growth, 10 mM $Mg^{+2}$ had little influence on NGF-mediated neurite growth but inhibited completely (p<0.01) the effect of R3 on enhancement of the NGF-mediated neurite growth response (Table 4), with no influence on cellular uptake of the peptide (Table 1). This effect was not due to a delay of the effect of R3 by $Mg^{+2}$ (data not shown).

To determine if the R3 peptide effect was mediated by a pertussis toxin sensitive mechanism, PC12 cells were pretreated prior to exposure to NGF and the R3 peptide. As depicted in Table 4, the presence of pertussis toxin did not influence the neurite growth-enhancing effect of the R3 peptide on NGF-mediated neurite growth.

Specificity of the R3 Peptide

The influence of R3 on growth factor-mediated neurite growth/survival was observed to be neurotrophin-specific. R3 had no influence on the survival effect of ciliary neurotrophic factor (CNTF) on ciliary neurons and no influence on basic fibroblast growth factor-mediated neurite growth by PC12 cells (Togari et al., 1985; Rydel and Greene, 1987) (data not shown).

Figure 7A:
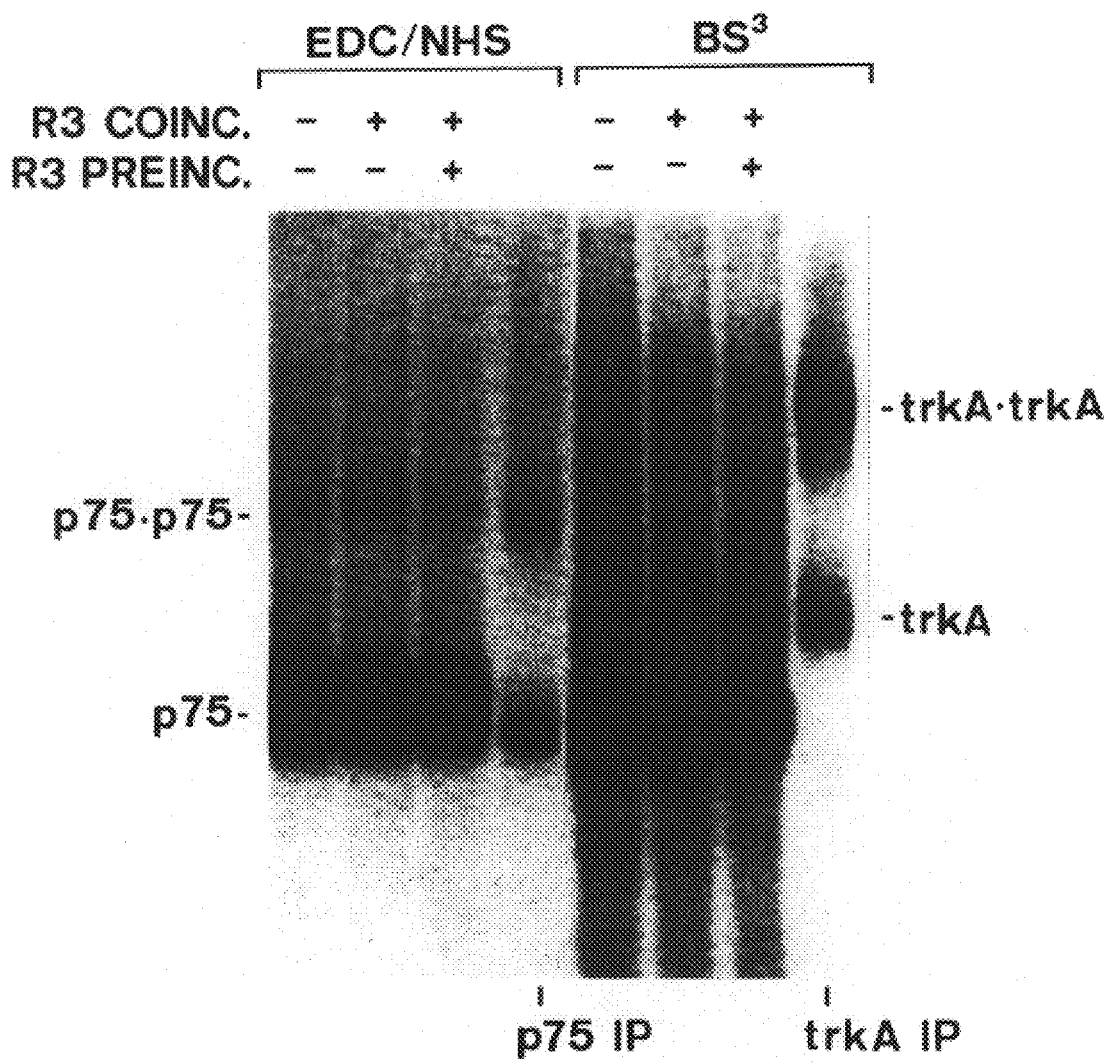
FIG. 7A illustrates the influence of peptide R3 on affinity cross-linking of TrkA and p75$^{NTR}$. Intact PC12 cells were treated with 50 μM R3 for 24 h (preinc.) in medium, harvested with CMF medium, and suspended at a concentration of $10^6 \cdot ml^{-1}$ (or $10^7 \cdot m^{-1}$ for immunoprecipitation studies) in HKR buffer. Cells were then incubated in the presence or absence of R3 (coinc.) for 15 min at 37° C. and cooled in ice. Cross-linking was performed by incubating cells with 1 nM [$^{125}$I]-NGF for 2 h at 4° C., adding EDC (5 nM) and NHS (2 mM) or BS$^3$ (0.4 mM) as indicated, and incubating for 30 min at 25° C. Cells were washed three times in HKR buffer and the pellet dissolved in reducing SDS sample buffer or in lysis buffer (1% NP-40, 10% glycerol, 1 mM PMSF, 10 μg-ml$^{-1}$ aprotinin, 1 μg/ml leupeptin, 0.5 M o-vanadate in TBS) for immunoprecipitation (lanes 4 and 8). For immunoprecipitation, the cellular debris was removed by centrifugation and the supernatant incubated with 1 μg anti-p75$^{NTR}$ monoclonal Ab 192 (Cedarlane Laboratories Ltd.) or 1 μg anti-TrkA polyclonal Ab (a gift from Dr. W. Mobley, University of California, San Francisco) for 4 h at 4° C. Immunoprecates were isolated by incubating with 50 μl of a 50% solution of protein A-SEPHAROSE™ (anti-Trk) or goat anti-mouse agarose (Ab 192) for 2 h at 4° C. Precipitates were washed 3 times in lysis buffer and dissolved in sample buffer. Samples were electrophoresed on 4% to 7.5% gradient SDS-polyacrylamide gels, dried and autoradiographed.
Figure 7B:
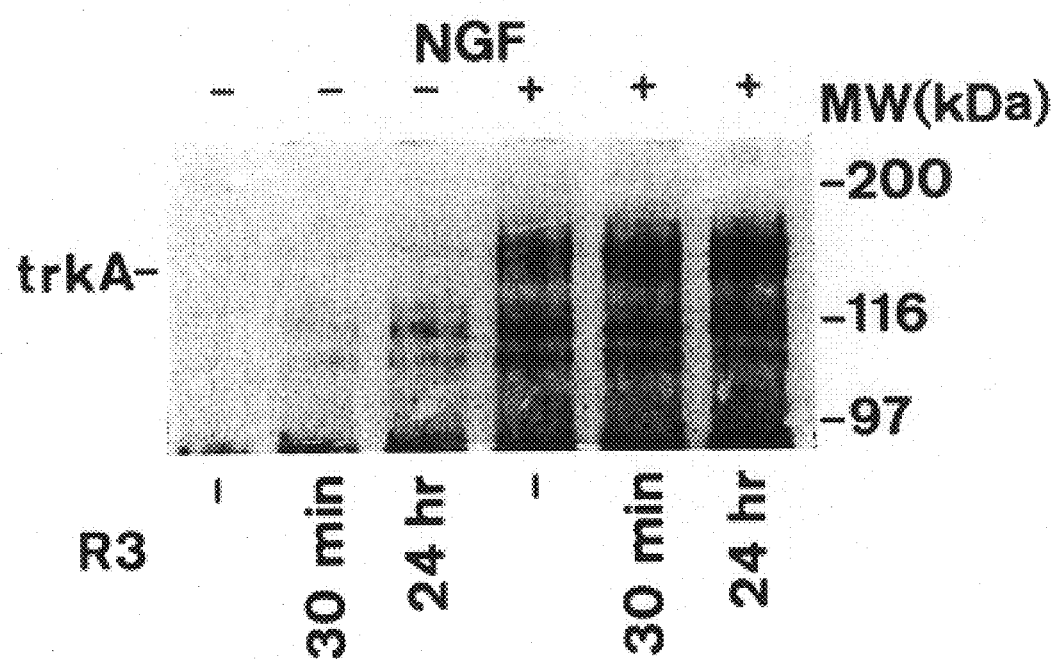
FIG. 7B illustrates the influence of peptide R3 on TrkA phosphorylation. PC12 cells were treated with R3 for 30 min or 24 h and suspended in HKR buffer at a concentration of $10^7 \cdot ml^{-1}$. NGF (50 ng·ml$^{-1}$) was added where indicated and samples incubated for 15 min at 37° C. Cells were subsequently harvested by centrifugation and the pellets dissolved in lysis buffer and immunoprecipitated for TrkA as described. Immunoprecipitated proteins were separated using 7.5% polyacrylamide gels (Laemmli) and transblotted to PVDF membrane. The membrane was processed for anti-phosphotyrosine with HRP-conjugated antibody RC-20 as described by the manufacture's literature (Transduction Laboratories Ltd.).

Influence of R3 Peptide on NGF Binding, Uptake, Receptor Affinity Cross-linking and TrkA Phosphorylation The influence of R3 on neurite growth did not involve a direct perturbation of binding of [$^{125}$I]NGF to PC12 cells; the peptide had no effect on steady-state total or non-displaceable binding when co-incubated with [$^{125}$I]NGF (data not shown). At low (20 pM) or high (0.2 nM) concentrations of [$^{125}$I]NGF, rates of [$^{125}$I]NGF uptake into PC12 or PC12$^{nnr5}$ cells were not influenced by the presence of saturating concentrations of R3 peptide, whether or not the peptide was presented to the cells 24 hours prior to and/or at the time of [$^{125}$I]NGF exposure (data not shown). Affinity cross-linking of [$^{125}$I]NGF to TrkA and p75$^{NTR}$ monomers or homodimers was not affected by the presence of the peptides (FIG. 7A), and R3 did not consistently influence NGF-mediated tyrosine phosphorylation of TrkA significantly either when used prior to or at the time of exposure of PC12 cells to NGF (FIG. 7B).

Discussion

Biological Studies

The present studies have extended to functional considerations, computational predictions first proposed by Feinstein and Larhammar (1990), and confirmed by Myers et al. (1994). A peptide (R3) corresponding to rat p75$^{NTR}$ 367–379, that part of the cytoplasmic region of p75$^{NTR}$ with highest $\mu_H$ value, indicating putative membrane-associating properties, enhanced temporally and transiently NGF-mediated neurite growth from rat PC12 pheochromocytoma cells and both chick and rat embryo sensory neurons in vitro when co-incubated with NGF. When incubated with PC12 cells prior to exposure to NGF, the R3 peptide inhibited transiently the NGF response. This peptide displayed cell associated behaviour consistent with compartmentalization in the cytoplasm of cells.

While R3 and other peptide analogues share biophysical and secondary structure properties with MP, the mechanism underlying transmembrane passage of these related peptides has not been elucidated by the present studies. The mechanism of translocation of certain peptides and MP, and of failure of R4 to translocate, may be analogous to the cytochrome P450 system, where transmembrane passage of this protein is determined by relationships between amino-terminal charged amino acid residues and hydrophobic stretches of the peptide (Sato, et al., 1990; Szczesna-Skorupa and Kemper, 1989). Such relationships are similar in R3, R9, R10, and MP, but quite different in R4 which has an 11-amino acid alpha-helical form containing no polar groups at the amino-terminal domain.

p75$^{NTR}$ 367–379 is a highly conserved domain of the common neurotrophin receptor (Large et al., 1989). Rat p75$^{NTR}$ 367–379 is identical to the human receptor in this region and differs by one cationic amino acid and one non-polar amino acid from the chick receptor. These differences were not sufficient to alter the biological properties of R3 since it was effective on rat tissue (PC12 and DRG) and on chick tissue (DRG) in enhancing NGF-mediated neurite growth.

Supportive evidence that $\mu_H$ and $H_n$ values and charged group relationships in p75$^{NTR}$ 367–379 contribute to NGF-mediated neurite growth was provided by observations where structural alterations of R3 were made. Such alterations did not change appreciably the CD spectrum, or relationships between charged groups and hydrophobic stretches, and did not alter cellular uptake. The peptide R9 differed from R3 by a single amino acid substitution, A-10 for R-10. This substitution altered $\mu_H$ and $H_n$ and the complementarity of charge relationships between R9 and p75$^{NTR}$ 367–379. The structural alteration provided by R9 influenced adversely its biological activity; by comparison, R9 had approximately 50–60% of the activity of R3 in influencing NGF-mediated neurite growth.

Peptide R10 substituted R-11 for I-11 in R3. This change did not alter the CD spectrum (FIG. 1) or cellular uptake (Table 1) of the peptide, but would be predicted to alter amphiphilicity by placing a hydrophilic group within a hydrophobic region of the alpha helix. Indeed, $\mu_H$ and $H_n$ values of R10 compared to R3 were 0.42, –0.54 and 0.75, 0.18 respectively. When this peptide was analyzed in biological assay, it had approximately 30% of the activity of R3 in influencing NGF-mediated growth.

The charged amino acids most complementary within p75$^{NTR}$ (and R3) and MP are p75$^{NTR}$ (D-368, R-375, R-376) and MP (K-4, K-11, K-12). Two cationic groups and one anionic group of R3 have distance and angular relationships similar, but not identical, to those relationships between three cationic groups in MP (Myers et al., 1994). Despite the CD spectra similarities of MP and R3 (and all peptide analogues), differences in $\mu_H$ and $H_n$ values (Eisenberg et al., 1984 a and b), the charge types and their relationships, plus the fourth cationic group (R-379) in the amphiphilic domain of R3 may explain why the biological response of R3 and MP differed with respect to neurite growth. As discussed in Myers et al., 1994, (incorporated herein by reference) the amphiphilic domains of p75$^{NTR}$ contain other charged residues that appear to confer higher degrees of functional specificity that potentially distinguish biological effects.

Notwithstanding the finding that MP was inactive in enhancing NGF-mediated neurite growth, the R3 peptide does possess some biochemical and biological properties displayed by MP. Magnesium is an inhibitor of the biochemical and biological activities of MP and related compounds (Higashijima et al., 1990; Lagunoff et al., 1983), and was also shown to inhibit the influence of the R3 peptide on NGF-mediated neurite growth. The R3 peptide effect appears not to involve a pertussis toxin-sensitive G-protein interaction, since this toxin had no influence on R3 peptide-mediated enhancement of NGF-induced neurite growth by PC12 cells. However, these observations do not exclude a G-protein-mediated phenomenon since pertussis-insensitive G-protein effects of MP have been observed (Nakahata et al. 1990).

Proposed Mechanism of Action of R3 Analogues in Neurite Growth

The modulatory influences of R3 and its analogues on neurite growth were determined by relative concentrations of TrkA and $p75^{NTR}$, and by relationships between peptide exposure and NGF exposure.

Neurite growth enhancement by R3 was observed with PC12 cells, but not with $PC12^{nnr5}$ cells which differ with respect to NGF responsiveness solely because of a low TrkA/$p75^{NTR}$ expression ratio (Loeb et al., 1991). Thus a function provided by TrkA was necessary to the response observed with R3 peptide. However, the influence of R3 on NGF-mediated neurite growth in co-incubation studies and on inhibition of neurite growth in pre-incubation studies was not mediated at the level of TrkA binding, or TrkA tyrosine phosphorylation, and did not involve perturbation of NGF uptake or the dose response profile for NGF-mediated neurite growth. These findings suggest that the influences of R3 and its analogues are mediated down-stream of early events in NGF signalling.

The finding that temporal relationships between cell exposure of R3 and NGF are determinants of neurite growth could suggest interactions between R3 and intracellular proteins or protein domains that are activated by liganded TrkA. It remains speculative whether such interactions occurring prior to TrkA ligand by NGF are inhibitory to subsequent downstream signalling involving complexing of intracellular proteins. However, candidate intracellular proteins that might be involved include the ERK protein kinases which interact with $p75^{NTR}$ (Volonte et al., 1993).

That both facilitatory and inhibitory effects of R3 on NGF-mediated neurite growth were transient might be explained at least in part by the presence of intracellular R3 in limiting concentrations, a tendency for the peptide to precipitate out of aqueous solution, and the constitutive turnover of putative cytoplasmic proteins with the potential to interact with the peptide.

The Role of the Common Neurotrophin Receptor in Neurite Growth

The findings of the present studies are consistent with a number of observations suggesting a role for $p75^{NTR}$ in NGF-mediated TrkA signalling. First, $p75^{NTR}$ is implicated in target innervation by sensory and sympathetic neurons in vivo (Lee et al., 1992), possibly by a left shift in the NGF dose response curve (Davies et al., 1993). Second, $p75^{NTR}$ accelerates TrkA-mediated differentiation responses in neuron-like sympathoadrenal cells (Verdi et al., 1994). Third, the cytoplasmic domain of $p75^{NTR}$ mediates NGF-specific biological effects (Yan et al., 1991). Finally, high-affinity binding and detection of both high MW (TrkA) and low MW ($p75^{NTR}$) receptors by NGF-affinity cross-linking is dependent upon the presence of cytoplasmic domains of $p75^{NTR}$ (Hempstead et al., 1990). Conclusions arising from these observations are relevant to the present studies and suggest that TrkA and p75 co-expression modulate NGF-mediated neurite extension. Further, an interaction yet to be elucidated between cytoplasmic domains of the two receptors is a determinant of expression of biologically relevant binding of NGF producing neurite growth.

With respect to the observations of Hempstead et al. (1990), only one of the deletion mutants eliminated the $p75^{NTR}$ 367–379 domain. This apparent discrepancy might be rationalized by the suggestion that the extensive deletion mutant described by Hempstead et al. (1990) would not permit $p75^{NTR}$ 367–379 to become immobilized via its hydrophobic domain in the cytoplasmic portion of the phospholipid membrane bilayer (Higashijima et al., 1983, 1990) because of steric hindrance effects produced by a receptor truncated in its cytoplasmic region between the transmembrane domain and the amphiphilic domain which is in proximity to the carboxy-terminus of $p75^{NTR}$. Implicit in this suggestion is that $p75^{NTR}$ is activated by NGF binding through a mechanism of receptor anchoring via its membrane-associating domain $p75^{NTR}$ 367–379 to the cytoplasmic plasma membrane.

The common neurotrophin receptor $p75^{NTR}$ has been implicated in apoptotic cell death in limiting conditions in the absence of ligand (Rabizadeh et al., 1993, incorporated herein by reference). The observation that the R3 peptide had no influence on survival of PC12 or $PC12^{nnr5}$ cells in limiting conditions in the absence or presence of NGF would tend to exclude the amphiphilic domain of $p75^{NTR}$ from a survival influence that is independent of TrkA function. Furthermore, because the biological function of the amphiphilic motif of $p75^{NTR}$ is not manifest in the absence of TrkA, it is likely that this domain is not primarily involved in activation of the sphingomyelin cycle (Dombrowsky et al., 1994). It is further contemplated by the inventors that the amphipathic compounds disclosed herein may modulate function of members of the NGF receptor superfamily.

PART B

A Distinctive Motif of the Common Neurotrophin Receptor $p75^{NTR}$ is a Binding Site for the Transcription Factor NFkB As mentioned in the Background Of The Invention, TNFR1 and $p75^{NTR}$ contain within their death domain regions, motifs that confer surface membrane associating properties as determined by maximum mean hydrophobic moment, and both signal translocation of transcription factor NFkB. In contrast, Apo-1/Fas, which contains a death domain but no amphiphilic sequence (Myers et al., 1994), does not translocate NFkB (Marsters et al., 1996). The inventors reasoned from these observations that the amphiphilic motif of $p75^{NTR}$ could be involved in NFkB activation/translocation, and thus conducted a series of experiments to determine whether the amphiphilic motif of $p75^{NTR}$ and NFkB interact directly. These studies were facilitated by the availability of, and studies with, R3 and related analogues disclosed in Part A above.

Materials and Methods

Materials

Synthetic peptides were provided by the Core Facility for Protein/DNA Chemistry, Queen's University, Kingston, Canada. "R3": LDALLAALRRIQR (SEQUENCE ID NO:1); "R9": LDALLAALRAIQR (SEQUENCE ID NO:2); and "R10": LDALLAALRRRQR (SEQUENCE ID NO:3). Tissue culture plastics were Corning/Costar obtained from Fisher Scientific. All chemicals and reagents were of the highest grade available and obtained from commercial sources.

Cell Culture

PC12 cells (Greene and Tischler, 1976), obtained from the American Type Culture Collection, and $PC12^{nnr5}$ (Loeb et al., 1991), were maintained in collagen coated culture flasks in RPMI 1640 (Gibco) supplemented with 10% heat-inactivated donor horse serum and 5% fetal calf serum (FCS) (Wisent) at 37° C. in 5% $CO_2$, 95% air. Upon weekly passage, the cells were split in a ratio of 1 to 10.

Assay of Neurite Growth

Dissociated cells enriched for sensory neurons from dorsal root ganglia (DRG) of ED8 chick were prepared as described in detail previously (Sutter et al., 1979). Cells were seeded into wells of Terasaki plates treated with poly-D-lysine at 900–1100 cells per well in supplemented Ham's F12 with 2.5% FCS and 0.25 ng/ml or 7.5 ng/ml NGF (Cedarlane) and the dc28-36 peptide at varying concentrations. The cells were incubated at 37° C. for 18 hrs and scored blind for neurite growth by counting all cells on the lower surface of the wells under phase contrast. A neurite was scored if its calibre from origin to terminal was approximately the same and it extended at least 1.5 cell diameters.

Preparation of Affinity Matrix

A peptide comprising the amphiphilic motif of the intracellular domain of $P75^{NTR}$ (R3) with six residues added to the N-terminus: KAYIAFLDALLAALRRIQR (SEQUENCE ID NO:4) was coupled at pH 7.0 to Aminolink (Pierce) agarose, according to the manufacturer's instructions. The putative transmembrane domain of $p75^{NTR}$ includes these six amino acid residues (Large et al., 1989).

Preparation of Affinity Purified Protein

PC12 cells were harvested and washed by 3 cycles of resuspension and centrifugation in $Ca^{2+}$, $Mg^{2+}$-free Gey's Balanced Salt Solution (CMF). The cell pellet was homogenized at a final cell concentration of $5 \times 10^6$ cells per ml, in 50 mM sodium phosphate pH 7.4 containing 2 mM EDTA, 0.25 mM sodium orthovanadate, 0.125% Lubrol and 1 mM PMSF (homogenizing buffer) with a Dounce homogenizer. The homogenate was centrifuged at 100,000×g for 30 min, and the resulting supernatant subjected to affinity chromatography. One bed volume of cell extract was loaded on the affinity gel equilibrated in homogenizing buffer, and allowed to interact with the gel for 1 h at room temperature. The column was then washed with 10 bed volumes of homogenizing buffer and 10 bed volumes of detergent-free homogenizing buffer. The bound material was then eluted with 0.5 mg/ml R3 peptide. The eluate was dialyzed (3500 cut off) extensively against 10 mM sodium phosphate pH 7.4 and taken to dryness under reduced pressure on a Speed Vac (Savant).

Electrophoresis and Immunoblotting

Proteins were fractionated on a 7.5% SDS-polyacrylamide gel (discontinuous system according to Laemmli (1970)), and transferred to nitrocellulose (Schleicher and Schuell). The membranes were probed with rabbit anti-NFkB p65 (1/500) (Santa Cruz) and the immune complexes detected with HRP-anti-rabbit IgG (1/2500) (Santa Cruz) and chemiluminescence (ECL Amersham) by exposure to HYPERFILM™ MP (Amersham) and manual processing.

Cross-linking

Y-R3 (5 μg) was labeled with 1 mCi of $Na^{125}I$ (Amersham) using iodobeads (Pierce) in 50 mM sodium phosphate buffer, as described in Part A. $^{125}I$-Y-R3 (0.5 μM) was incubated with PC12 cell extract (prepared as above) or affinity purified proteins at pH 7.0, with and without a 150-fold molar excess of competing unlabeled peptide for 2 hrs at 4° C. At that time, EDC (Pierce) and NHS (Pierce) were added to a final concentration of 2 mM each and the reaction allowed to proceed for 30 min at room temperature. The reaction was quenched by adding Tris-HCl to a final concentration of 50 mM. An aliquot was removed and mixed with 4 volumes of SDS sample buffer for SDS-PAGE and the remainder subjected to immunoprecipitation.

Immunoprecipitation

Cell extract or R3 affinity purified material was incubated for 4 hrs at 4° C. with 5 μl of agarose conjugated goat anti-NFkB p65 (Santa Cruz). The gel was washed at 4° C. with 5×1 ml of HKR containing 1% NP40, followed by a final wash without detergent. SDS reducing sample buffer was added to the gel and the samples were heated at 95° C. for 5 minutes prior to electrophoresis as described above.

Results

Figures 8A, 8B, 8C:
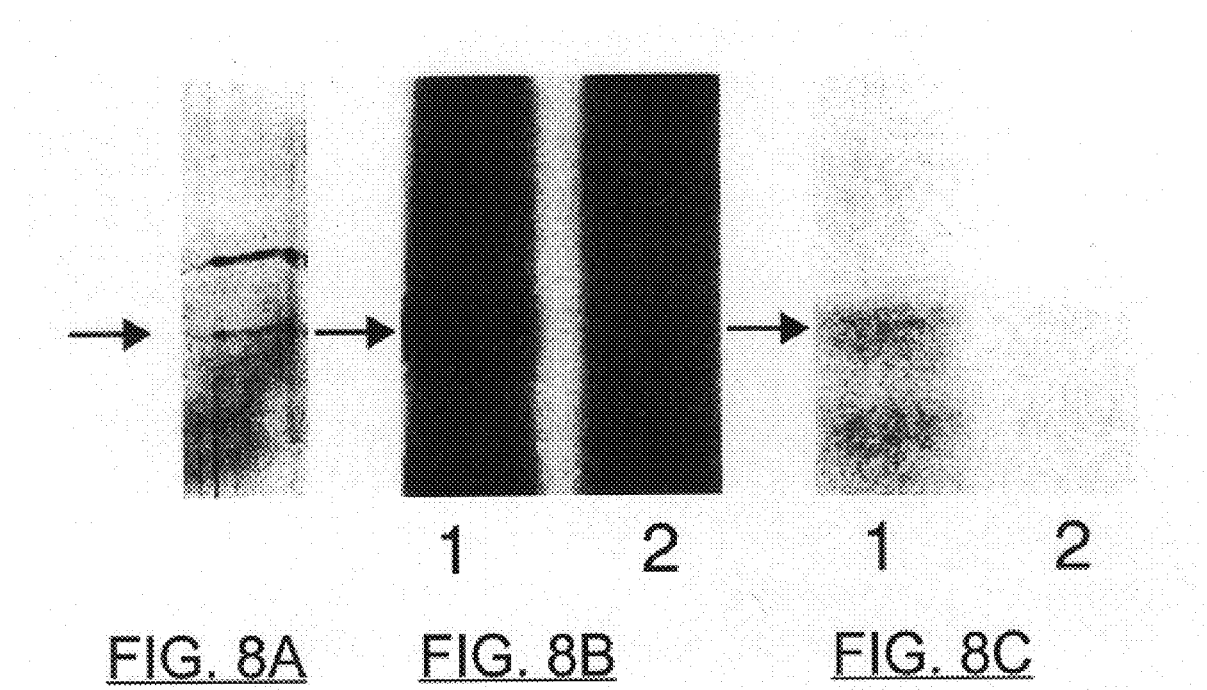
FIG. 8 presents data showing protein interacting with an intracellular domain of p75$^{NTR}$:
A. Material eluted from the affinity matrix bearing the R3 peptide separated on a 7.5% SDS gel and silver stained. Arrow shows position of the 65 kDa species. B. and C. $^{125}$I-Y-R3 was cross-linked to whole PC12 cell extract without (lane 1) or with (lane 2) a 150-fold excess of unlabeled R3. B: separation of the mixture on a 7.5% SDS-polyacryamide gel followed by autoradiography; C: immunoprecipitation with anti-NFkB-agarose (Santa Cruz) prior to SDS-polyacrylamide gel electrophoresis (SDS-PAGE) and autoradiography, arrows show position of 65 kDa species.

A soluble extract of PC12 cells was applied to the R3 affinity resin. SDS-PAGE with silver staining (Oakley et al. 1980) of the material recovered from the column by elution with R3 peptide in solution revealed two major components. Estimation of the molecular size of the proteins from their migration gave a molecular weight of 68,000±4300 for one protein and 79,800±3500 for the second (n=7, M±SEM) from a plot of log M against $R_f$ of high and low range prestained (BioRad) and/or unstained (Pharmacia) molecular weight markers (FIG. 8A). A similar profile was obtained when extracts from "primed" (exposed to 100 ng/ml NGF for 10 days) PC12 cells, $PC12^{nnr5}$ cells or ED9 chick brain were used. These proteins were not recovered by chromatography of extract on glycine-coupled SEPHAROSE beads, all other steps being identical, nor when elution from the R3 affinity matrix was attempted with an unrelated peptide of comparable size.

The R3 peptide with N-terminal tyrosine was found to have biological properties parallel to its parent compound as described in Part A. Radio-iodination of Y-R3 provided a labeled probe for this motif of the intracellular domain of $P75^{NTR}$. Chemical cross-linking of this peptide with a soluble PC12 extract revealed a species with an apparent molecular weight of 65 kDa that interacted specifically with this motif (FIG. 8B).

Figures 9A, 9B:
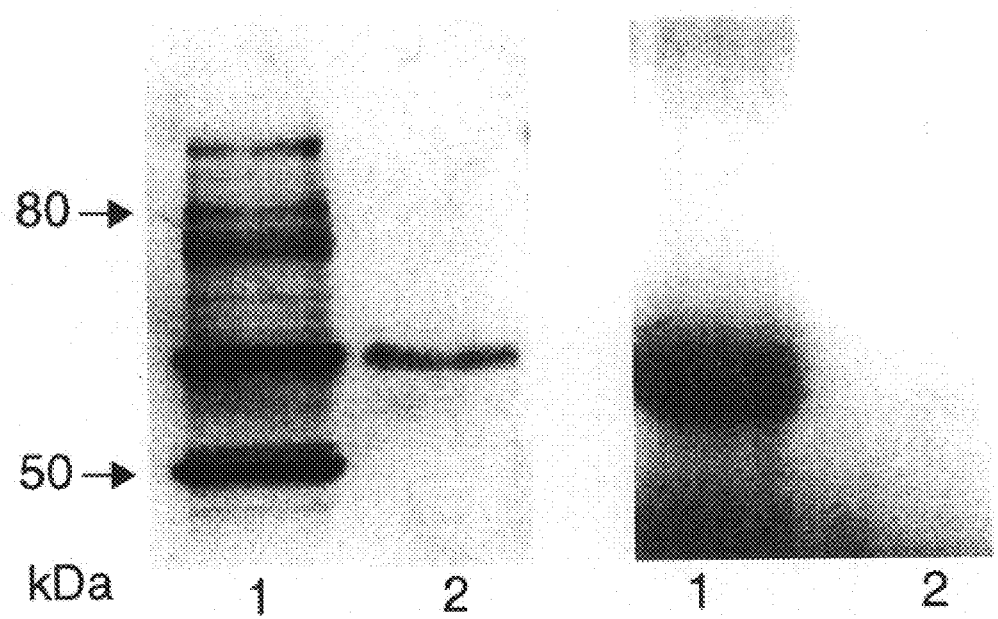
FIG. 9 presents data confirming detection of the p65 subunit of NFkB:
A. PC12 soluble extract (lane 1) and R3-affinity purified extract (lane 2) were separated by SDS-PAGE, transferred to nitrocellulose and probed with rabbit anti-NFKB p65 (Santa Cruz) (1:5000), followed by HRP-goat anti-rabbit IgG (1:2500) and chemiluminescent detection (ECL Amersham).
B. Affinity purified PC12 extract chemically cross-linked to $^{125}$I-Y-R3 in the absence (lane 1) or presence (lane 2) of 150-fold molar excess of unlabeled R3, followed by immunoprecipitation with agarose-conjugated goat anti-NFkB (Santa Cruz), separation as in A, and detection by autoradiography.

The p65 subunit of NFkB was detected in PC12 soluble extracts and in the R3-affinity purified material (FIG. 9A). This 65 kDa protein could also be specifically cross-linked to the iodinated probe for the intracellular domain of $P75^{NTR}$, the interaction being displaced by a 150-fold molar excess of unlabeled peptide, and the complex immunoprecipitated by antibodies to the transcription factor (FIGS. 9B and 8C).

To examine the structural specificity of the interaction of R3 peptide with the 65 kDa species, PC12 cell soluble extract was chemically cross-linked with 0.5 μM $^{125}I$-Y-R3 in the absence and presence of a 150-fold molar excess of unlabeled R9 or R10. R9, which comprises amphiphilic domain with alanine substituted in position 10, exhibited 61% of the biological activity of R3 in vitro; R10, which has an arginine substitution in position 11, was shown above to have 29% of the biological activity of R3. The reaction mixtures were separated by SDS-PAGE, followed by autoradiography. Densitometric scanning of the film revealed that the intensity of the radioactive band migrating at 65 kDa was reduced by the unlabeled peptides and parallelled their in vitro biological activity, with R9 displacing 76% and R10 displacing 43% of the radiolabel.

Figure 10:
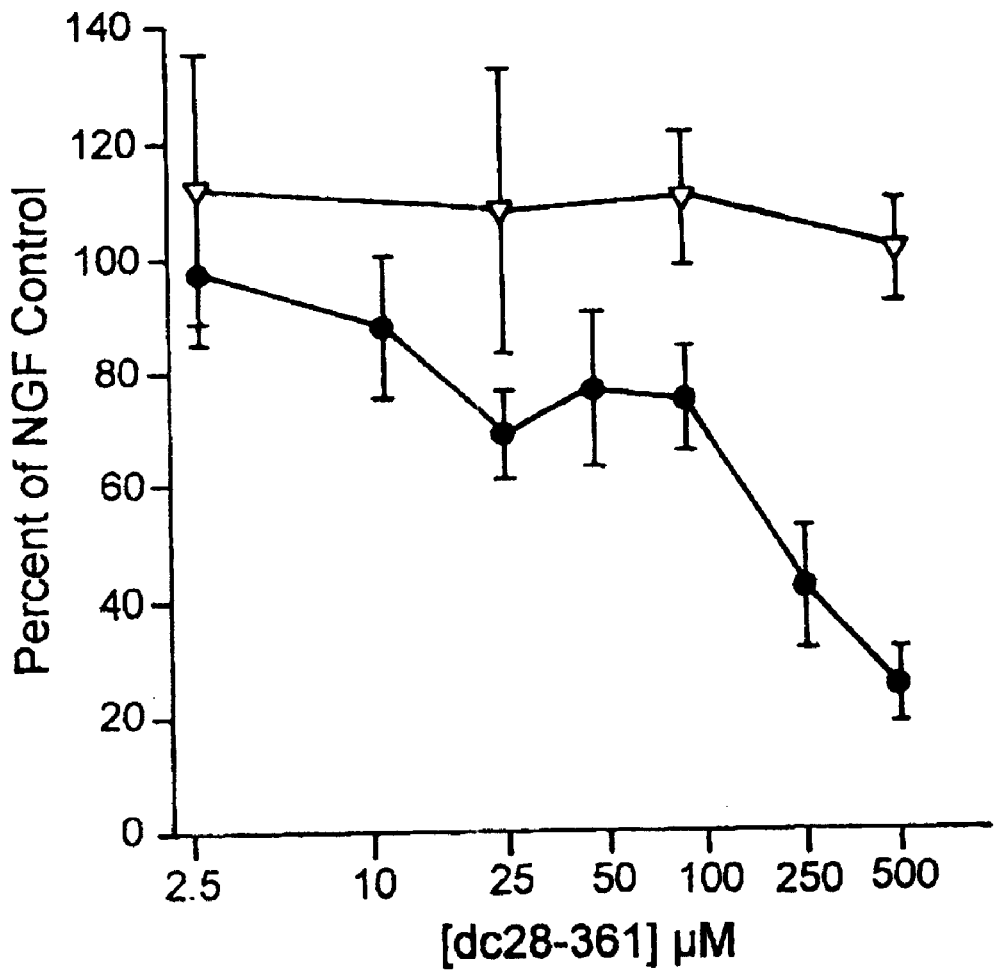
FIG. 10 is a plot demonstrating inhibition of neurite growth by a p75-selective peptide: effect of a peptide mimic of the p75-interactive motif of NGF on neurite growth by ED8 DRG neurons in the presence of: ●0.25 ng/ml NGF or ▽7.5 ng/ml NGF. Bioassays were scored at 18–20 hours after seeding. Data points are the mean of three experiments, error bars reflect the standard error of the mean.

To confirm a role for $p75^{NTR}$ in NGF-mediated neurite growth, the inventors utilized a conformationally constrained peptide mimic (dc28-36) of a $p75^{NTR}$ binding domain of NGF that has been shown previously to selectively interfere with NGF binding and cross-linking to $p75^{NTR}$, and to mimic the effect of the null mutation of the $p75^{NTR}$ receptor on neuronal survival in vivo (Van der Zee et al., 1996, incorporated herein by reference). FIG. 10 demonstrates a concentration-dependent inhibition of NGF-mediated neurite growth by primary sensory neurons in vitro in the presence of peptide dc28-36 at 10 pM, but not at 300 pM NGF.

Discussion

The principal observation emerging from the present studies is the finding that the transcription factor NFkB interacts directly and specifically with a mimic of a $p75^{NTR}$ receptor motif that was shown in Part A to enhance NGF-mediated growth in cells bearing both p75 and TrkA receptors. That the interaction between NFkB and synthetic amphiphilic peptides mimics that observed in the functional studies on NGF-mediated neurite growth with R3 analogues, taken together with the finding that a p75 selective peptide antagonist of NGF inhibits NGF-mediated neurite growth, has led the inventors to conclude that the $p75^{NTR}$/NFkB interaction is likely involved in signalling NGF-mediated neurite growth and, further, that the effect is most dramatic in limiting NGF concentrations.

NFkB is the prototypic member of a family of transcription factors that are maintained in a latent state in cell cytoplasm, and are translocated to the nucleus upon activation (Baeuerle and Henkel, 1994; Karin and Hunter, 1995). The inactive state of NFkB is a complex comprising an inhibitor IkB which, when phosphorylated by an as yet uncharacterized kinase, dissociates from NFkB and a related 50 kDa protein (see Karin and Hunter, 1995 for review). Such proposed mechanism neither implies nor excludes the direct interactions between a receptor motif and NFkB that have been demonstrated in the present studies. However, a precedent for such direct receptor/transcription factor interactions emerges from observations with Notch receptor and the transcription factor RBP-Jk/Su(H) (Tamura et al., 1995).

While other members of the TNF receptor family, specifically CD40 and TNFR1, signal NFkB activation by interactions with structurally related proteins of the TRAF family, such proteins have yet to be implicated in $p75^{NTR}$ activation of NFkB (see Bothwell, 1996 for review). The present studies do not exclude $p75^{NTR}$ interactions with a TRAF-like protein for NFkB activation, and they are not inconsistent with such an interaction, particularly if a TRAF-like protein/NFkB complex binds (likely via NFkB) to the amphiphilic motif of $p75^{NTR}$. Of interest to the present studies is the observation that, while the $p75^{NTR}$ amphiphilic domain mimic interacts directly with NFkB, CD40 activation of NFkB apparently does not use this specific mechanism, since the intracellular domain of CD40 does not contain alpha-helices (Myers et al., 1994) or a death domain (Marsters et al., 1996). These observations might suggest that NFkB can be activated in three ways: via a TRAF-family member (e.g., CD40), via an amphiphilic motif (e.g., $p75^{NTR}$), or via both mechanisms (e.g., TNFR1). In addition, there may be domains on TRAF that share at least secondary structural features with the amphiphilic domain of $p75^{NTR}$ (367–379) that is mimicked by the R3 peptide. The restricted ability of neurotrophins, all of which bind to $p75^{NTR}$, to activate NFkB (Carter et al., 1996) might be explained by lack of redundancy in signalling pathways converging on NFkB. Indeed, if is as suggested here, the amphiphilic motif of $p75^{NTR}$ is involved in NGF-mediated neurite growth via NFkB, such a mechanism would serve to enhance both the specificity of neurotrophin-mediated activation, and its sensitivity, which has been reported (Chao and Hempstead, 1995, incorporated herein by reference).

A role for the amphiphilic motif of $p75^{NTR}$ in NGF-mediated neurite growth in TrkA-positive cells was described in Part A. That the effects of analogues of R3, the peptide mimic of $p75^{NTR}$, in enhancing responsiveness of PC12 cells and primary sensory neurons of chick to the neurite growth-promoting properties of limiting concentrations of NGF is similar to the rank ordering of displacement of $^{125}$I-R3 cross-linking to NFkB, provides strong correlative evidence that NFkB can be involved in signalling neurite growth in TrkA/p75—positive cells. Further support for this idea emerges from the observation that a $p75^{NTR}$-selective peptide mimic of NGF, (dc28-36), which we have shown blocks the pro-apoptotic effects of $p75^{NTR}$ in vivo (Van der Zee et al., 1996), has been shown here to inhibit NGF-mediated neurite growth by primary sensory neurons in vitro in conditions of limiting neurotrophin. A role for a NFkB/$p75^{NTR}$ interaction in neurite growth is consistent with NFkB activation of adhesion proteins (Baeuerle and Henkel, 1994), with $p75^{NTR}$ induction of the L1 adhesion protein (Seilheimer and Schachner, 1987), with $p75^{NTR}$-mediated cell migration (Anton et al., 1994), and neural crest tumor metastasis (Marchetti et al., 1996), and suggests that TrkA and $p75^{NTR}$ signalling may converge on cytoskeletal elements affecting cell migratory phenomena mediating neurite growth.

Based on these observations, it is reasonable to suggest that, whereas the TrkA signalling pathway is sufficient to mediate neurite growth, $p75^{NTR}$ accelerates responsiveness to NGF when this receptor is co-expressed via a NFkB-mediated signalling event. As such, $p75^{NTR}$ may play a role in signalling a differentiation event (neurite growth) in limiting concentrations of neurotrophin both by rendering TrkA a high affinity receptor (see Chao and Hempstead, 1995 for review), and by signalling via NFkB.

PART C

Design of Peptides and Peptidomimetics as Analogues of R3

Moreover, the invention is not limited to peptide analogues of R3. Rather, the invention encompasses any compound with amphipathic properties wherein a first face of the compound is able to associate with or be anchored in a cell membrane and a second face displays charged or polar moieties, wherein the compound enhances the effect of a neurotrophin. In some embodiments of the invention, the compound is a small molecule. In some embodiments, the compound comprises a polymer portion; any convenient polymer backbone may be employed.

As previously discussed, in Morgan et al., 1989 (incorporated herein by reference), peptide mimetics are defined as "structures which serve as appropriate substitutes for peptides in interactions with receptors and enzymes. The mimetic must possess not only affinity, but also efficacy and substrate function." For purposes of this disclosure, the terms "peptidomimetic" and "peptide mimetic" are used interchangeably according to the above-excerpted definition. That is, a peptidomimetic exhibits function(s) of a peptide, without restriction of structure. Peptidomimetics of the present invention, i.e., analogues of R3, may include amino acid residues or other moieties which provide the functional characteristics described herein.

As described previously, R3 can be taken up by cells. The ability to be taken up by cells is desirable for compounds of the invention. In some embodiments, a compound of the invention may have structural characteristics that permit it to be taken up directly. In other embodiments, a compound of the invention may be linked to a carrier that permits uptake by cells. When inside the cell, certain carriers dissociate from the compound having R3-like properties. Certain other carriers are chemically cleaved from the compound having R3-like properties.

Figure 12:
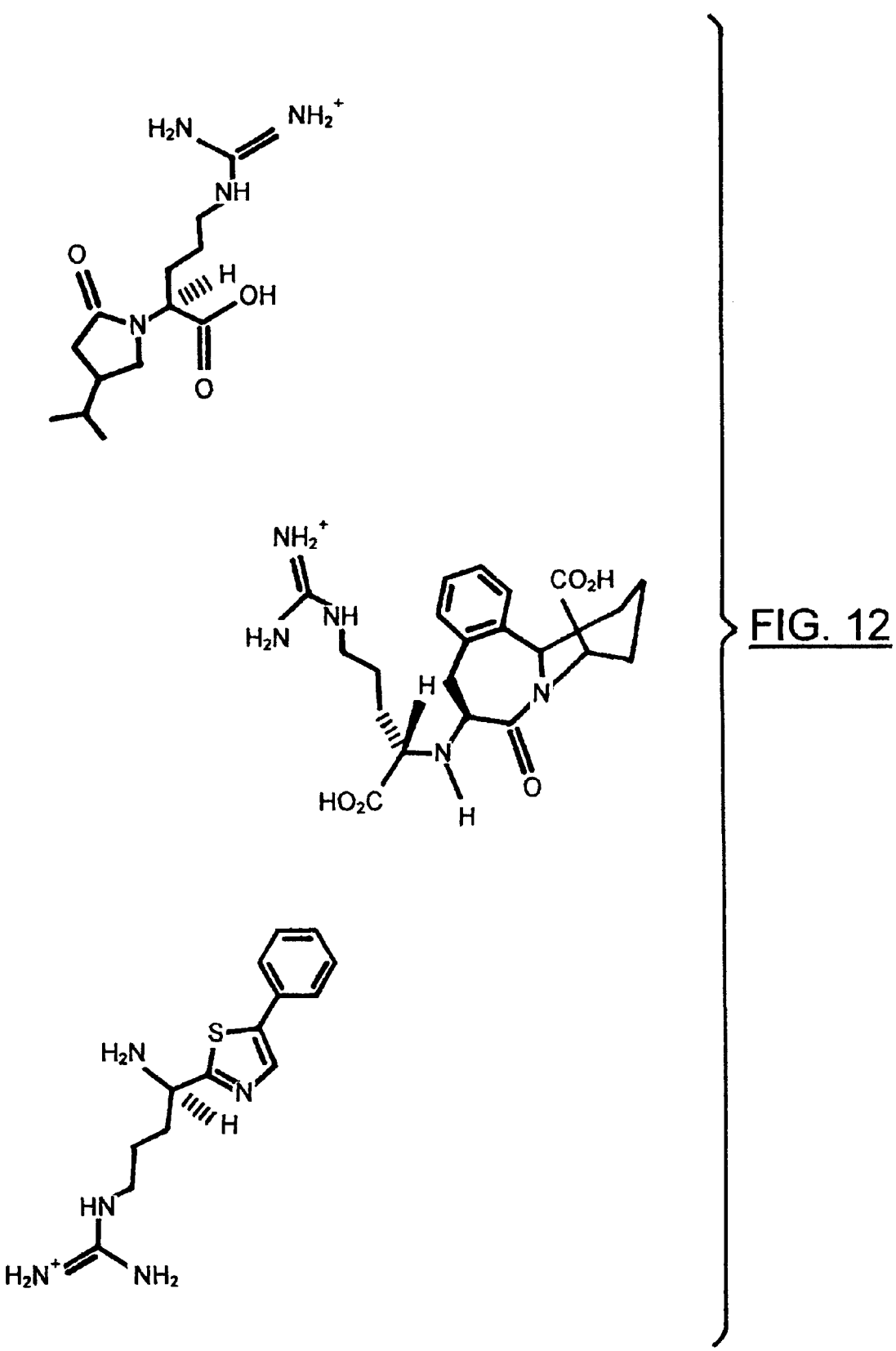
FIG. 12 illustrates three more prophetic examples of peptidomimetics as analogues of R3.

Below, the inventors provide prophetic examples of compounds of the invention. Compounds of this type may be employed in methods of the invention. FIGS. 11A and 11B illustrate non-limiting prophetic examples of peptidomimetics contemplated by the inventors to enhance neurotrophin effects according to the present invention. In FIG. 11A, the various side chains (R-groups) shown include L (leucine), R (arginine), D (aspartic acid), F (phenylalanine), K (lysine) and I (isoleucine), and "α" indicates the position that an α-carbon of an amino acid would occupy relative to the side chain. Inside the 5-membered ring, "R" denotes right-handed chirality of the indicated carbon. FIG. 11B illustrates the same molecules as FIG. 11A but shows the amino acid side chains fully drawn. FIG. 12 illustrates three more examples of prophetic peptidomimetics in accordance with the present invention.

Those skilled in the art will understand that the examples of FIGS. 11A and 11B are simply representative peptidomimetics and that the invention is in no way limited to these compounds. For example, conservative substitutions of the amino acid side chains are possible, demonstrated by the positively charged side chains K and R being substituted for one another in the Figure. Similarly, negatively charged side chains may be substituted for each other, i.e., E (glutamic acid) for D (aspartic acid). Small hydrophobic side chains such as those of amino acids I (isoleucine), L (leucine) and A (alanine) may be substituted for each other. Large hydrophobic ringed side chains of amino acids F, Y (tyrosine) and W (tryptophan) may be substituted for each other. In addition, the present invention is not limited only to amino acid side chains at these positions, but other moieties with similar characteristics may be substituted therefor.

TABLE 1

Uptake of [$^{125}$I] peptide by PC12 cells

| Tyrosinated peptide | Additive to culture medium | Time at half-maximal uptake (min) | Saturating uptake (pmol/10$^6$/ cells)[a] |
|---|---|---|---|
| Y-R3 | — | 30 | 48.1 ± 7.6 |
| Y-R3 | MgCl$_2$(10 mM) | 30 | 55.5 ± 15.5 |
| Y-R9 (YLDALLAALRAIQR) | — | 30 | 59.0 ± 8.1 |
| Y-R10 (YLDALLAALRRRQR) | — | 30 | 43.6 ± 7.5 |
| R4 | — | 0 | 0 |

The concentration of peptide in solution was 10 μM.
[a]Mean ± SEM, n = 4; non-chaseable.

TABLE 2

Survival of PC12 and PC12$^{nmr5}$ cells in serum-free medium

| Additives | PC12 (% of control) | PC12$^{nmr5}$ (% of control) |
|---|---|---|
| None | 0.247 ± 0.049 | 0.591 ± 0.047 |
| Pre-R3[b] (10 μM) | 0.235 ± 0.049 | 0.592 ± 0.031 |
| Co-R3[c] (10 μM) | 0.284 ± 0.048 | 0.575 ± 0.024 |
| NGF (50 ng/ml) | 0.926 ± 0.084 | 0.490 ± 0.042 |

TABLE 2-continued

Survival of PC12 and PC12$^{nmr5}$ cells in serum-free medium

| Additives | PC12 (% of control) | PC12$^{nmr5}$ (% of control) |
|---|---|---|
| Pre-R3 (10 μM) + NGF (50 ng/ml) | 0.904 ± 0.089 | 0.527 ± 0.030 |
| Co-R3 (10 μM) + NGF (50 ng/ml) | 0.720 ± 0.060 | 0.526 ± 0.020 |

PC12: the number of surviving cells in serum-free medium supplemented with 50 ng/ml NGF was not significantly different from control. The presence of R3 peptide did not significantly alter the number of viable cells maintained in the presence or absence of NGF. PC12$^{nmr53}$: the viability of these cells in serum-free medium was significantly less than its serum-containing control. However, there were no significant differences between the treatments under serum-free conditions.
[a]'Control' consisted of sister wells of cells (PC12 or PC12$^{nmr5}$) maintained in serum-containing medium where the presence of NGF (50 ng/ml) did not significantly alter the number of surviving cells (P = 0.96 by t-test).
[b]Pre-R3 (10 μM) signifies that the cells were exposed the peptide in the presence of serum for 24 h prior to changeover to serum-free conditions, as well as during the indicated treatment.
[c]Co-R3 (10 μM) signifies the addition of R3 peptide at start of treatment.

TABLE 3

| Peptide Response[3] | Sequence | μH[1] | H$_n$[2] | % of Control DRG[4] |
|---|---|---|---|---|
| R3 | LDALLAALRRIQR | 0.75 | 0.18 | 100 ± 16 |
| R9 | -----------A--- | 0.66 | 0.10 | 61 ± 1[5] |
| R10 | ------------R-- | 0.42 | −0.54 | 29 ± 4[5] |

[1]maximum mean hydrophobic moment, as per Eisenberg et al. (1984)
[2]H$_n$ mean hydrophobicity at μH, as per Kyte and Doolittle (1982)
[3]M ± SEM of response calculated as: peptide with NGF-NGF alone X100 R3 with NGF - NGF alone
[4]n = 3 assays scored at 43, 44, and 48 hours with replicates of 6, 4, and 3 wells, respectively, for each addition
[5]p < 0.05 versus control

TABLE 4

| NGF | Additive | R3 (10 μM) | % of NGF response (mean ± SEM) |
|---|---|---|---|
| +[a] | — | — | 100 ± 13 |
| +[a] | Mg$^{2+}$ (10 mM) | — | 133 ± 7 |
| +[a] | — | + | 247 ± 13 |
| +[a] | Mg$^{2++}$ | + | 120 ± 7 |
| +[b] | — | — | 100 ± 10 |
| + | — | + | 240 ± 40 |
| + | PT[c] | + | 200 ± 9 |

[a]Scored at 30 h following NGF addition.
[b]Scored at 44 h following NGF addition.
Pertussis toxin (100 ng/ml) preincubation for 48 h.

Abbreviations

| NGF | nerve growth factor |
|---|---|
| p75$^{NTR}$ | common neurotrophin receptor |
| MP | mastoparan |
| PC12 | rat pheochromocytoma cell line |
| PC12$^{nmr5}$ | PC12 mutant cell line expressing low levels of TrkA |
| Trk | tyrosine receptor kinase. |
| TrkA | receptor tyrosine kinase family member A |
| BDNF | brain-derived neurotrophic factor |
| NT-3 | neurotrophin-3 |
| NT-4/5 | neurotrophin-4/5 |
| NT-6 | neurotrophin-6 |
| CH$_3$CN | acetonitrile |
| CD | circular dichroism |
| MTT | [3-(4,5-Demethylthiazol-2-yl)-2,5-diphenyltetrazolium bromide] |

-continued

| | |
|---|---|
| CO₂ | carbon dioxide |
| ED | embryonic day |
| BSA | bovine serum albumin |
| HKR | Hepes-Krebs-Ringer |
| PAGE | polyacrylamide gel electrophoresis |
| SDS | sodium dodecyl sulphate |
| CMF | Ca$^{++}$-Mg$^{++}$-free phosphate buffer |
| DRG | dorsal root ganglion |
| GTP | guanosyl triphosphate |
| CNTF | ciliary neurotrophic factor |
| R3 | peptide homologue of rat p75$^{NTR}$ 367–379; other R peptides are analogues of R3 |
| NHS | N-hydroxysulphosuccinimide |
| BS3 | bis-(sulphosuccinimidyl) suberate |
| PMSF | phenyl-methyl-sulphonyl fluoride |
| HRP | horseradish peroxidase |
| PT | pertussis toxin |
| EDC | 1-ethyl-3-(3-methylaminopropyl) carbodiimide |
| NFkB | nuclear factor kappa B |
| TNF | tumor necrosis factor |

References

Ananthanarayanan, V. S., Saint-Jean, A., and Jiang, P. (1992) Conformation of a synthetic hexapeptide substrate of collagen lysyl hydroxylase. *Arch. Biochem. Biophys.* 298, 21–28.

Anton E. S. Weskamp G., Reichardt L. F. and Matthew, W. D. (1994) Nerve growth factor and its low-affinity receptor promote Schwann cell migration. *Proc. Nat. Acad. Sci. USA* 91, 2795–2799.

Baeuerle P. A. and Henkel, T. (1994) Function and activation of NFkB in the immune system. *Annu. Rev. Immunol.* 12, 141–179.

Bernd, P. and Greene, L. A. (1984) Association of $^{125}$I-nerve growth factor with PC12 pheochromocytoma cells. Evidence for internalization via high-affinity receptors only and for long-term regulation by nerve growth factor of both high- and low-affinity receptors. *J. Biol. Chem.* 259, 15509–15516.

Bothwell, M. (1996). p75$^{NTR}$: A receptor after all. *Science* 272, 506–507.

Carter B. D., Kaltschmidt C., Kaltschmidt B., Offenhauser N., Bohm-Matthaei R., Baeuerle P. A. and Barde Y.-A. (1996) Selective activation of NFkB by nerve growth factor through the neurotrophin receptor p75. *Science* 272, 542–545.

Chao, M. V. and Hempstead, B. L. (1995). p75 and Trk: A two-receptor system. *Trends Neurosci.* 18, 321–326.

Connolly, D. T., Knight, M. B., Harakas, N. K., Wittwer, A. J. and Feder, J. (1986) Determination of the number of endothelial cells in culture using an acid phosphatase assay. *Anal. Biochem.* 152, 136–140.

Davies, A. M. Lee, K. F. and Jaenisch, R. (1993) p75-deficient trigeminal sensory neurons have an altered response to NGF but not to other neurotrophins. *Neuron* 11, 565–574.

Dombrowsky, R. T., Werner, M. H., Castellino, A. M., Chao, M. V. and Hannum, Y. A. (1994) Activation of the sphingomyelin cycle through the low-affinity neurotrophin receptor. *Science* 265, 1596–1599.

Drevon, C. A., Berg, T. and Norum, K. R. (1977) Uptake and degradation of cholesterol ester-labelled rat plasma lipoproteins in purified rat hepatocytes and nonparenchymal liver cells. *Biochem. Biophys. Acta* 487, 122–136.

Eisenberg, D., Schwarz, E., Komaromy, M. and Wall, R. (1984a) Analysis of membrane and surface protein sequences with the hydrophobic moment plot. *J. Mol. Biol.* 179, 125–142.

Eisenberg, D., Weiss, R. M. and Terwilliger, T. C. (1984b) The hydrophobic moment detects periodicity in protein hydrophobicity. *Proc. Natl. Acad. Sci. USA* 81, 140–144.

Feinstein, D. L. and Larhammar, D. (1990) Identification of a conserved protein motif in a group of growth factor receptors. *FEBS Lett.* 272, 7–11.

Gill, J. Higgins, T. and Rozengurt, E. (1991) Mastoparan, a novel mitogen for Swiss$^{3T3}$ cells, stimulates pertussis toxin-sensitive arachidonic acid release without inositol phosphate accumulation. *J. Cell Biol.* 113, 943–950.

Gotz, R., Koster, R., Winkler, C., Raulf, F., Lottspeich, F., Schartl, M. and Thoenen, H. (1994) Neurotrophin-6 is a new member of the nerve growth factor family. *Nature* 372, 266–269.

Greene L. A. and Tischler A. S. (1976). Establishment of a noradrenergic clonal line of rat adrenal pheochromocytoma cells which respond to nerve growth factor. *Proc. Natl. Acad. Sci. USA* 73, 2424–2428.

Harlow, E. and Lane, D. (1988) *Antibodies: A Laboratory Manual*. Cold Spring Harbor Laboratory, Cold Spring Harbor, N.Y.

Hempstead, B. L., Patil, N., Thiel, B. and Chao, M. V. (1990) Deletion of cytoplasmic sequences of the nerve growth factor receptor leads to loss of high affinity ligand binding. *J. Biol. Chem.* 265, 9595–9598.

Heumann, R. (1994) Neurotrophin signalling. *Curr. Opin. Neurobiol.* 4, 668–679.

Higashijima, T., Wakamatsu, K., Takemitsu, M., Fujino, M., Nakajima, T. and Miyazawa, T. (1983) Conformational change of mastoparan from wasp venom on binding with phospholipid membrane. *FEBS Lett.* 152, 227–230.

Higashijima, T., Burnier, J. and Ross, E. M. (1990) Regulation of Gi and Go by mastoparan, related amphiphilic peptides, and hydrophobic amines. Mechanism and structural determinants of activity. *J. Biol. Chem.* 265, 14176–14186.

Huang B., Eberstadt M., Olejniczak E., Mendows R. And Fesik S. (1996) NMR structure and mutagenesis of the Fas(Apo-1/CD95) death domain. *Nature* 384, 638–641.

Ibanez, C. F., Ilag, L. L., Murray-Rust, J. and Persson, H. (1993) An extended surface of binding to Trk tyrosine kinase receptors in NGF and BDNF allows the engineering of a multifunctional pan-neurotrophin. *EMBO J.* 12, 2281–2293.

Kaplan, D. R., Martin-Zanca, D. and Parada, L. F. (1991a) Tyrosine phosphorylation and tyrosine kinase activity of the trk proto-oncogene product induced by NGF. *Nature* 350, 158–160.

Kaplan, D. R., Hempstead, B. L., Martin-Zanca, D., Chao, M. V., and Parada, L. F. (1991b) The trk proto-oncogene product: a signal transducing receptor for nerve growth factor. *Science* 252, 554–558.

Karin M. and Hunter T. (1995) Transcriptional control by protein phosphorylation: signal transmission from the cell surface to the nucleus. *Curr. Biol.* 5, 747–757.

Krammer, P. H. and Debatin, K-M. (1992) When apoptosis fails. *Curr. Biol.* 2, 383–385.

Kyte, J. and Doolittle, R. F. (1982) A simple method for displaying the hydropathic character of a protein, *J. Mol. Biol.* 157, 105–132.

Laemmli, U. K. (1970) Cleavage of structural proteins during the assembly of the head of bacteriophage T4. *Nature* 227, 680–685.

Lagunoff, D., Martin, T. and Read, G. (1983) Agents that release histamine from mast cells. *Annu. Rev. Pharmacol. Toxicol.* 23, 331–351.

Large, T. H., Weskamp, G., Helder, J. C., Radeke, M. J., Misko, T. P., Shooter, E. M. and Reichardt, L. F. (1989) Structure and developmental expression of the nerve growth factor receptor in the chicken central nervous system. *Neuron* 2, 1123–1134.

Lee, K-F., Li, E., Huber, L. J., Landis, S. C., Sharpe, A. H., Chao, M. V. and Jaenisch, R. (1992) Targeted mutation of the gene encoding the low affinity NGF receptor p75 leads to deficits in the peripheral nervous system. *Cell* 69, 737–749.

Lee, K-F., Davies, A. M. and Jaenisch, R. (1994a) p75-deficient embryonic dorsal root sensory and neonatal sympathetic neurons display a decreased sensitivity to NGF. *Development* 120, 1027–1033.

Lee, K-F., Bachman, K., Landis, S. and Jaenisch, R. (1994b) Dependence on p75 for innervation of some sympathetic targets. *Science* 263, 1447–1449.

Loeb, D. M., Maragos, J., Martin-Zanca, D., Chao, M. V. and Greene, L. A. (1991) The trk proto-oncogene rescues NGF responsiveness in mutant NGF-nonresponsive PC12 lines. *Cell* 66, 961–966.

Lopresti, P., Poluha, W., Poluha, D. K., Drinkwater, E. and Ross, A. H. (1992) Neuronal differentation triggered by blocking cell proliferation. *Cell Growth Differ.* 3, 627–635.

Mallett, S. and Barclay, A. N. (1991) A new superfamily of cell surface proteins related to the nerve growth factor receptor. *Immunol. Today* 12, 220–223.

Marchetti D., McQuillan D. J., Spohn W. C., Carson D. D. and Nicolson G. L. (1996) Neurotrophin stimulation of human melanoma cell invasion: selected enhancement of heparanase activity and heparanase degradation of specific heparan sulfate subpopulations. *Cancer Res.* 56, 2856–2863.

Marsters S. C., Sheridan J. P., Donahue C. J., Pitti R. M., Gray C. L., Goddard A. D., Bauer K. D. and Ashkenazi A. (1996) Apo-3, a new member of the tumor necrosis factor receptor family, contains a death domain and activates apoptosis and NFkB. *Curr. Biol.* 6, 1669–1676.

Mobley, W. C., Schenker, A. and Shooter, E. M. (1976) Characterization and isolation of proteolytically modified nerve growth factor. *Biochemistry* 15, 1543–1551.

Morgan, B. A. and Gainor, J. A. (1989) Approaches to the discovery of non-peptide ligands for peptide receptors and peptidases. In *Annual Reports in Medicinal Chemistry* (Vinick, F. J., ed.) pp. 243–252, Academic Press, San Diego, Calif.

Mossman, T. (1983) Rapid colorimetric assay for cellular growth and survival: application to proliferation and cytotoxicity assays. *J. Immunol. Methods* 65, 55–63.

Myers, S. M., Ross, G. M., Dostaler, S. M., Anderson, M. N., Weaver, D. F. and Riopelle, R. J. (1994) Putative cytoplasmic amphiphilic domains in the nerve growth factor receptor superfamily. *Biochim. Biophys. Acta* 1196, 21–28.

Nakahata, N., Tamiko Abe, M., Matsuoka, I. and Nakanishi, H. (1990) Mastoparan inhibits phosphoinositide hydrolysis via pertussis toxin-insensitive G-protein in human astrocytoma cells. *FEBS Lett.* 260, 91–94.

Oakley, B. R., Kirsch D. R. and Morris N. R. (1980) A simplified ultrasensitive silver stain for detecting proteins in polyacrylamide gels. *Anal. Biochem.* 105, 361–363.

Rabizadeh, S., Oh, J., Zhong, L., Yang, J., Bitler, C. M., Butcher, L. L. and Bredesen, D. E. (1993) Induction of apoptosis by the low-affinity NGF receptor. *Science* 261, 345–348.

Rydel, P. E. and Greene, L. A. (1987) Acidic and basic fibroblast growth factors promote stable neurite outgrowth and neuronal differentiation in cultures of PC12 cells. *J. Neurosci.* 7, 3637–3653.

Sato, T., Sakaguchi, M., Mihara, K. and Omura, T. (1990) The amino-terminal structures that determine topological orientation of cytochrome P-450 in microsomal membrane. *EMBO J.* 9, 2391–2387.

Seilheimer B. and Schachner M. (1987) Regulation of neural cell adhesion molecule expression on cultured mouse Schwann cells by nerve growth factor. *EMBO J.* 6, 1611–1616.

Sutter, A., Riopelle, R. J., Harris-Warrick, R. M. and Shooter, E. M. (1979a) The heterogeneity of nerve growth factor receptors. In *Progress in Clinical and Biological Research* 31: *Transmembrane Signalling* (M. Bitensky, R. J. Collier, D. F. Steiner and C. F. Fox, eds.) pp. 659–677, Alan R. Liss Inc., New York.

Sutter, A., Riopelle, R. J., Harris-Warrick, R. M. and Shooter, E. M. (1979b) Nerve growth factor receptors. *J. Biol. Chem.* 254, 5972–5982.

Szczesna-Skorupa, E. and Kemper, B. (1989) $NH_2$-terminal substitutions of basic amino acids induce translocation across the microsomal membrane and glycosylation of rabbit cytochrome P450IIC2. *J. Cell Biol.* 108, 1237–1243.

Tamura K., Taniguchi Y., Minoguchi S., Sakai T., Tun T., Furukawa T. and Honjo T. (1995) Physical interaction between a noval domain of the receptor Notch and the transcription factor RBP-Jk/Su(H). *Curr. Biol.* 5, 1416–1423.

Togari, A., Dickens, G., Kuzuya, H. and Guroff, G. (1985) The effect of fibroblast growth factor on PC12 cells. *J. Neurosci.* 5, 307–316.

Ueda, Y., Walsh, E., Nakanishi, H. and Yoshida, K. (1994) A colorimetric assay method for the evaluation of neurotrophic activity in vitro. *Neuroscience Letters* 165, 203–207.

Verdi, J. M., Birren, S. J., Ibanez, C. F., Persson, H., Kaplan, D. R., Benedetti, M., Chao, M. V. and Anderson, D. J. (1994) $p75^{LNGFR}$ regulates Trk signal transduction and NGF-induced neuronal differentiation in MAH cells. *Neuron* 12, 733–745.

Volonte, C., Anagelastro, J. M. and Greene, L. A. (1993) Association of protein kinases ERK1 and ERK2 with p75 nerve growth factor receptors. *J. Biol. Chem.* 268, 21410–21415.

Van der Zee C. E. E. M., Ross G. M., Riopelle R. J. and Hagg T. (1996). Survival of cholinergic forebrain neurons in developing $p75^{NGFR}$-deficient mice. *Science* 274, 1729–1732.

Yan, H., Schlessinger, J. and Chao, M. V. (1991) Chimeric NGF-EGF receptors define domains responsible for neuronal differentiation. *Science* 252, 561–563.

Therefore what is claimed is:

1. A method for enhancing NGF-mediated cell growth or survival, comprising:

exposing cells expressing TrkA, in the presence of NGF, to an amphipathic peptide or peptidomimetic wherein said peptide or peptidomimetic is p75$^{NTR}$ 367–379 (SEQ ID NO: 1) or a variant thereof which has a mean hydrophobic moment ($\mu_H$) of about 0.4, wherein $\mu_H$ is calculated using the formula:

$$\mu_H = \left(\left[\sum_{n=1}^{N} H_n \sin\delta_n\right]^2 + \left[\sum_{n=1}^{N} H_n \cos\delta_n\right]^2\right)^{1/2}$$

where N is the number of amino acid residues, $H_n$ is the hydrophobicity of the nth amino acid residue, $\delta_n = 2\pi n/m$, where $\delta_n$ is the angle in radians at which the nth side chain emerges from the helical axis, and m is the number of residues per turn, wherein said peptide or peptidomimetic enhances NGF-mediated cell growth or survival.

2. The method according to claim 1 wherein said cells are of a neuronal lineage.

3. The method according to claim 2 wherein said growth or survival comprises neurite growth.

4. The method according to claim 1 wherein said peptide or peptidomimetic comprises a sequence of about eleven amino acid residues.

5. The method according to claim 1 wherein said peptide or peptidomimetic comprises about four charged or polar moieties.

6. The method according to claim 1 wherein said peptide or peptidomimetic comprises an amino acid sequence selected from the group consisting of LDALLAALRRIQR (SEQ ID NO: 1), LDALLAALRAIQR (SEQ ID NO: 2) and LDALLAALRRRQR (SEQ ID NO: 3).

7. A method for enhancing NGF-mediated cell growth or survival, comprising:

exposing cells expressing p75$^{NTR}$, in the presence of NGF, to an amphipathic peptide or peptidomimetic wherein said peptide or peptidomimetic is p75$^{NTR}$ 367–379 (SEQ ID NO: 1) or a variant thereof which has a mean hydrophobic moment ($\mu_H$) of about 0.4, wherein $\mu_H$ is calculated using the formula:

$$\mu_H = \left(\left[\sum_{n=1}^{N} H_n \sin\delta_n\right]^2 + \left[\sum_{n=1}^{N} H_n \cos\delta_n\right]^2\right)^{1/2}$$

where N is the number of amino acid residues, $H_n$ is the hydrophobicity of the nth amino acid residue, $\delta_n = 2\pi n/m$, where $\delta_n$ is the angle in radians at which the nth side chain emerges from the helical axis, and m is the number of residues per turn, wherein said peptide or peptidomimetic enhances NGF-mediated cell growth or survival.

8. The method according to claim 7 wherein said cells are of a neuronal lineage.

9. The method according to claim 8 wherein said growth or survival comprises neurite growth.

10. The method according to claim 7 wherein said peptide or peptidomimetic comprises a sequence of about eleven amino acid residues.

11. The method according to claim 7 wherein said peptide or peptidomimetic comprises about four charged or polar moieties.

12. The method according to claim 7 wherein said peptide or peptidomimetice comprises an amino acid sequence selected from the group consisting of LDALLAALRRIQR (SEQ ID NO: 1), LDALLAALRAIQR (SEQ ID NO: 2) and LDALLAALRRRQR (SEQ ID NO: 3).

13. A method for enhancing NGF-mediated cell growth or survival, comprising:

exposing cells expressing TrkA, in the presence of NGF, to a compound selected from the group consisting of:

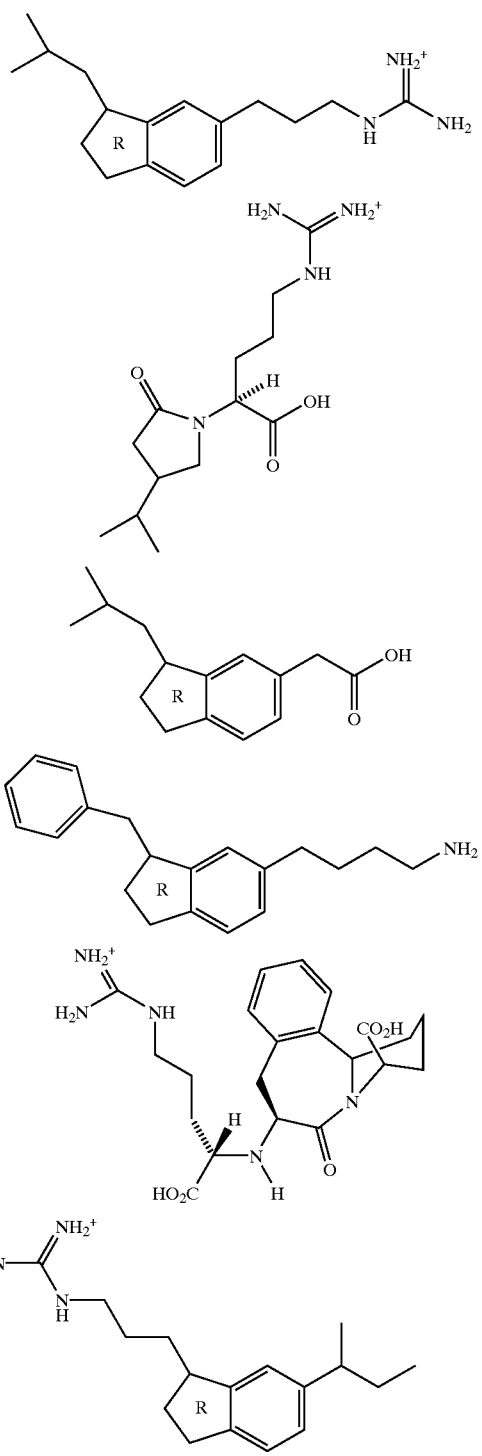

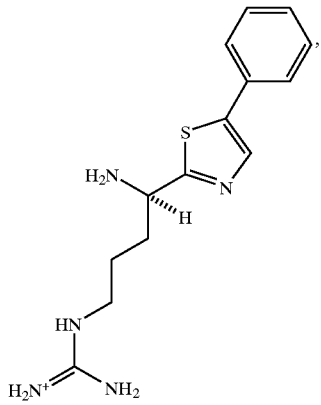

wherein growth and/or survival of said cells is enhanced relative to cells not exposed, in the presence of NGF, to said compound.

14. The method according to claim 13 wherein said cells are of a neuronal lineage.

15. The method according to claim 14 wherein said growth or survival comprises neurite growth.

16. A method for enhancing NGF-mediated cell growth or survival, comprising:

exposing cells expressing p75$^{NTR}$, in the presence of NGF, to a compound selected from the group consisting of:

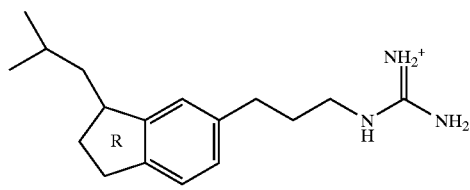

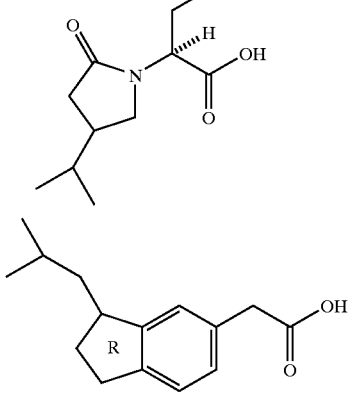

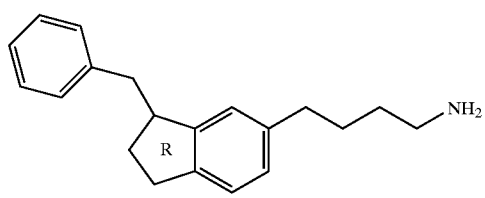

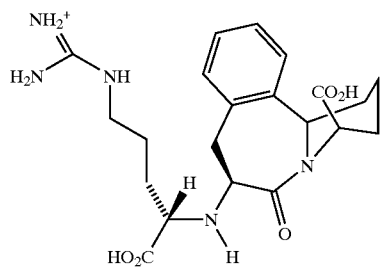

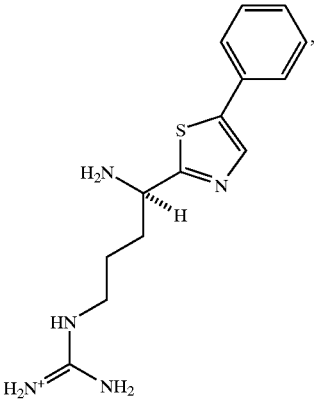

and

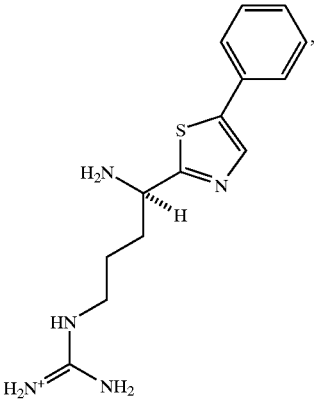

wherein growth and/or survival of said cells is enhanced relative to cells not exposed, in the presence of NGF, to said compound.

17. The method according to claim 16 wherein said cells are of a neuronal lineage.

18. The method according to claim 17 wherein said growth or survival comprises neurite growth.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (iii) HYPOTHETICAL: NO (ix) FEATURE
       (D) OTHER INFORMATION: SEQ ID NO:1 comprises an
           amphiphilic motif of the intracellular domain of
           p75NTR and corresponds to the 13 amino acid
           peptide which is described as R3 in the present
           application.

(xi) SEQUENCE DESCRIPTION: SEQ ID NO: 1:

Leu Asp Ala Leu Leu Ala Ala Leu Arg Arg Ile Gln Arg
 1               5                  10

(2) INFORMATION FOR SEQ ID NO: 2:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (iii) HYPOTHETICAL: NO (ix) FEATURE
       (D) OTHER INFORMATION: SEQ ID NO:2 is an analogue
           of R3 wherein an alanine residue at position 10
           replaces the arginine residue at position 10 in R3.
           This sequence is described as R9 in the present
           application.

(xi) SEQUENCE DESCRIPTION: SEQ ID NO: 2:

Leu Asp Ala Leu Leu Ala Ala Leu Arg Ala Ile Gln Arg
 1               5                  10

(2) INFORMATION FOR SEQ ID NO: 3:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (iii) HYPOTHETICAL: NO (ix) FEATURE
            (D) OTHER INFORMATION: SEQ ID NO:3 is an analogue
                of R3 wherein an arginine residue at position 11
                replaces the isoleucine residue at position 11 in
                R3. This sequence is described as R10 in
                the present application.

(xi) SEQUENCE DESCRIPTION: SEQ ID NO: 3:

Leu Asp Ala Leu Leu Ala Ala Leu Arg Arg Arg Gln Arg
 1               5                  10

(2) INFORMATION FOR SEQ ID NO: 4:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: peptide (iii) HYPOTHETICAL: NO (ix) FEATURE
            (D) OTHER INFORMATION: SEQ ID NO:4 comprises
                the 13 amino acid peptide R3 (SEQ ID NO:1)
                coupled via its amino terminus to six amino acid
                residues of the transmembrane domain of p75NTR
                (Large et al., (1989) Structure and Developmental
                Expression of the Nerve Growth Factor Receptor
                in the Chicken Central Nervous System, Neuron 2,
                1123-1134) for use in an affinity matrix as
                described in the present application.

(xi) SEQUENCE DESCRIPTION: SEQ ID NO: 4:

Lys Ala Tyr Ile Ala Phe Leu Asp Ala Leu Leu Ala Ala Leu Arg Arg
 1               5                  10                  15

Ile Gln Arg (2) INFORMATION FOR SEQ ID NO: 5:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (iii) HYPOTHETICAL: NO (ix) FEATURE
            (D) OTHER INFORMATION: SEQ ID NO:5 corresponds to
                the tetradecapeptide mastoparan (MP) known in the
                literature (Myers et al., (1994) Putative
                Cytoplasmic Amphiphilic Domains in the Nerve Growth Factor/Tumour Necrosis Factor Receptor Superfamily,
Biochimica et Biophysica Acta,1196,21-28).

(xi) SEQUENCE DESCRIPTION: SEQ ID NO: 5:

```
Ile Asn Leu Lys Ala Leu Ala Ala Leu Ala Lys Lys Ile Leu
1               5                   10
```

(2) INFORMATION FOR SEQ ID NO: 6:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: peptide (iii) HYPOTHETICAL: NO (ix) FEATURE
      (D) OTHER INFORMATION: SEQ ID NO:6 is a tyrosinated
         analog of R3 (SEQ ID NO:1).

(xi) SEQUENCE DESCRIPTION: SEQ ID NO: 6:

```
Tyr Leu Asp Ala Leu Leu Ala Ala Leu Arg Arg Ile Gln Arg
1               5                   10
```

(2) INFORMATION FOR SEQ ID NO: 7:

(i) SEQUENCE CHARACTERISTICS:

(A) LENGTH: 24 amino acids
      (B) TYPE: amino acid
      (C) STRANDEDNESS: single
      (D) TOPOLOGY: linear (ii) MOLECULE TYPE: peptide (iii) HYPOTHETICAL: NO (ix) FEATURE
      (D) OTHER INFORMATION: SEQ ID NO:7 comprises an
         11-amino acid peptide homologue of the inner
         transmembrane domain of p75NTR (Large et al.,(1989)
         Structure and Developmental Expression of
         the Nerve Growth Factor Receptor in the Chicken
         Central Nervous System, Neuron 2, 1123-1134)
         linked to the 13-amino acid peptide R3 (SEQ ID NO:1)
         via the amino terminus of R3, and corresponds to
         the 24 amino acid peptide which is described as R4
         in the present application.

(xi) SEQUENCE DESCRIPTION: SEQ ID NO: 7:

```
Val Val Val Gly Leu Val Ala Tyr Ile Ala Phe Leu Asp Ala Leu  Leu
1               5                   10                  15

Ala Ala Leu Arg Arg Ile Gln Arg
            20
```